United States Patent
Langner et al.

(10) Patent No.: US 9,206,146 B2
(45) Date of Patent: Dec. 8, 2015

(54) PURIFICATION OF POSACONAZOLE AND OF POSACONAZOLE INTERMEDIATES

(75) Inventors: Martin Langner, Kundl/Tyrol (AT); Dominic De Souza, Holzkirchen (DE); Abhinay C. Pise, Navi Mumbai (IN); Sachin Bhuta, Navi Mumbai (IN)

(73) Assignee: SANDOZ AG, Basel (CH)

( * ) Notice: Subject to any disclaimer, the term of this patent is extended or adjusted under 35 U.S.C. 154(b) by 77 days.

(21) Appl. No.: 13/697,803

(22) PCT Filed: May 18, 2011

(86) PCT No.: PCT/EP2011/058039
§ 371 (c)(1),
(2), (4) Date: Mar. 27, 2013

(87) PCT Pub. No.: WO2011/144657
PCT Pub. Date: Nov. 24, 2011

(65) Prior Publication Data
US 2013/0211086 A1    Aug. 15, 2013

(30) Foreign Application Priority Data

May 19, 2010 (EP) .................................. 10163210

(51) Int. Cl.
*C07D 307/12* (2006.01)
*C07D 405/06* (2006.01)
*C07D 405/12* (2006.01)

(52) U.S. Cl.
CPC ............ *C07D 307/12* (2013.01); *C07D 405/06* (2013.01); *C07D 405/12* (2013.01)

(58) Field of Classification Search
CPC ............................ C07D 249/08; C07D 241/04
USPC ........................................ 544/366; 548/268.8
See application file for complete search history.

(56) References Cited

U.S. PATENT DOCUMENTS

| | | | |
|---|---|---|---|
| 4,957,730 A | 9/1990 | Bohn et al. | |
| 5,403,937 A | 4/1995 | Saksena et al. | |
| 5,486,625 A * | 1/1996 | Leong et al. | 549/448 |
| 5,595,872 A | 1/1997 | Wetterau | |
| 5,693,626 A | 12/1997 | Saksena et al. | |
| 5,710,154 A | 1/1998 | Saksena et al. | |
| 5,714,490 A | 2/1998 | Saksena et al. | |
| 5,834,472 A | 11/1998 | Sangekar et al. | |
| 5,972,381 A | 10/1999 | Sangekar et al. | |
| 6,355,801 B1 | 3/2002 | Giesinger et al. | |
| 6,958,337 B2 | 10/2005 | Andrews et al. | |
| 2010/0197621 A1 | 8/2010 | Henry et al. | |

FOREIGN PATENT DOCUMENTS

| | | | | |
|---|---|---|---|---|
| EP | 0736030 A1 | 10/1996 | | |
| EP | 1230231 B1 | 8/2002 | | |
| EP | 01394162 | 3/2004 | | |
| WO | 9309114 | 5/1993 | | |
| WO | 9425452 A1 | 11/1994 | | |
| WO | WO 9425452 A1 * | 11/1994 | ........... | C07D 405/06 |
| WO | 9516658 A1 | 6/1995 | | |
| WO | 9517407 A1 | 6/1995 | | |
| WO | 2006007540 | 1/1996 | | |
| WO | 9633163 | 10/1996 | | |
| WO | 9633178 | 10/1996 | | |
| WO | 9638443 | 12/1996 | | |
| WO | 9700255 A1 | 1/1997 | | |
| WO | 9722579 | 6/1997 | | |
| WO | 9722710 A1 | 6/1997 | | |
| WO | 9733178 | 9/1997 | | |
| WO | 9918097 | 4/1999 | | |
| WO | 0280678 | 10/2002 | | |
| WO | 2005/075473 | 1/2005 | | |
| WO | 2005117831 | 12/2005 | | |

(Continued)

OTHER PUBLICATIONS

Serajuddin, Abu. Advanced Drug Delivery Reviews 59 (2007)603-616.*
Reichardt, Christian. Solvents and Solvent Effects in Organic Chemistry. 3rd ed. Wiley-VCH. (2004). 418-421.*
Blundell et al., Synlett 1994, pp. 263-265.
Brown et al., J. Chem. Soc. 2003, 125 (36), 10808-10809.
Cordova et al., Chem. Eur. J. 2004, 10 (15), 3673-3684.
Di Santo et al., "antifungal estrogen-like imidazoles. Synthesis and antifungal activities of thienyl and 1H-pyrrolyl derivatives of 1-aryl-2-(1H-imidazol-1-yl)ethane", European Journal of Medicinal Chemistry, Editions Scientifique Elsevier, Paris, FR, vol. 32, No. 2, Jan. 1, 1997, pp. 143-149.
Greene et al., Protective Groups in Organic Synthesis:, 2nd ed., John Wiley & Sons, New York 1991 10-142.
Greene et al., Protective Groups in Organic Synthesis:, 3rd ed., Wiley-Interscience (1999).

(Continued)

*Primary Examiner* — Golam M M Shameem
*Assistant Examiner* — Laura Daniel
(74) *Attorney, Agent, or Firm* — Jeffrey S. Melcher; Manelli Selter PLLC

(57) ABSTRACT

The present invention relates to a process for the preparation of a hydrogen chloride (HCl) salt of a compound of formula (I) wherein $Y_1$ and $Y_2$ are independently F or Cl, preferably F, said compound of formula (I) containing the cis-isomer and the trans-isomer, wherein the process comprises (1) providing the compound of formula (I) comprised in a first suitable solvent; and (2) treating the compound of formula (I) comprised in the first suitable solvent with HCl comprised in a second suitable solvent to obtain the HCl salt of the compound of formula (I).

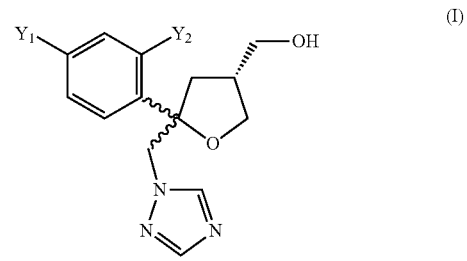

37 Claims, 1 Drawing Sheet

(56) References Cited

FOREIGN PATENT DOCUMENTS

| WO | 2007/122156 | 4/2007 |
|---|---|---|
| WO | 2007/143390 | 12/2007 |
| WO | 2008/136279 | 4/2008 |
| WO | 2009/058267 | 10/2008 |
| WO | 2009/141837 | 5/2009 |
| WO | 2009/129297 | 10/2009 |
| WO | 2010000668 | 1/2010 |
| WO | 2011/144653 | 11/2011 |
| WO | 2011/144655 | 11/2011 |
| WO | 2011/144656 | 11/2011 |
| WO | 2013/186320 | 12/2013 |

OTHER PUBLICATIONS

Hayashi et al., J. Org. Chem. 2005, 69 (18), 5966-5973.
Hepperle et al., Tetrahedron Lett. 2002, 43, 3359-3363.
Huang et al., Organic Letters 2004, 6 (25) 4795-4798.
Kurome et al., "Total Synthesis of an Antifungal Cyclic Depsipeptide Aureobasidin A", Tetrahedron, Elsevier Science Publishers. Amsterdam, NL, vol. 52, No. 12. Mar. 18, 1996, pp. 4327-4346.
Na Y-M et al., "Synthesis and antifungal activity of new 1-halogenbenzyl-3-imidazoly 1methylindole derivatives", European Journal of Medicinal Chemistry, Editions Scientifique Elsevier, Paris, FR, vol. 38, No. 1, Jan. 1, 2003, pp. 75-87.
Peterson, "Carbonyl olefination reaction using silyl-substituted organometallic compounds", J. Org. Chem (1968) 33 (2) pp. 780-784.
Remington's Pharmaceutical Sciences, 15th Ed., Mack Publishing Co., New Jersey (1991).
Saksena et al., Tetrahedron Lett. 2004, 45 (44), 8249-8251.
Tetrahedron Letters 32 (1991). pp. 7545-7548.
Xianhai Huang et al., "Manipulation of N,O-Nucleophilicity: Efficient Formation of 4-N-Substituted 2,4-Dihydro-3H-1, 2, 4-Triazolin-3-ones", Organic Letters, American Chemical Society, US, vol. 6, No. 25, Nov. 10, 2004, pp. 4795-4798.
International Search Report and Written Opinion Mailed Sep. 9, 2011 in PCT/EP2011/058035.
International Search Report and Written Opinion Mailed Aug. 4, 2011 in PCT/EP2011/058036.
International Search Report and Written Opinion Mailed Aug. 5, 2011 in PCT/EP2011/058039.
International Search Report and Written Opinion Mailed Jul. 13, 2011 in PCT/EP2011/058033.
Weicheng Thou et al., Survey of Syntheses of Azole Antifungals. Chinese Journal of Pharmaceuticals, vol. 37, No. 2, pp. 125-133, Dec. 31, 2006.
Sixi Wang, Synthesis of SIPI-4678 and Voriconazole, The Master Degree Theses of the Shanghai Institute of Parmaceutical Industry, pp. 10-13, Mar. 2007.
Sixi, Wang, Synthesis of SIPI-4678 and Voriconazole, The Master Degree Theses of the Shanghai Institute of Pharmaceutical Industry, pp. 9-17, Jan. 24, 2007.
Chinese Office Action issued in Application No. 201180024340.2, Mar. 24, 2014, pp. 1-13, and translation.
Chinese Office Action issued in Application No. 201180024363.3, Jan. 17, 2014, pp. 1-7, and translation.
Chinese Office Action issued in Application No. 201180024632.6, May 20, 2014, pp. 1-10, and translation.
Robert V. Hoffman, Organic Chemistry: An Intermediate Text, Second Edition, John Wiley & Sons, Inc., 2004, p. 128.
Parmee, "Human beta3 adreneergic receptor containing cyclic ureidobenzenesulonafides," Bioorganic & Medicinal Chemistry Letters, vol. 9, 1999, pp. 749-745, XP002648199.
Written Opinion issued in PCT/EP2012/061346, WO2012/172015, Jun. 20, 2013, pp. 1-5.
International Search Report issued in PCT/EP2013/062298, WO2013/186320, Feb. 8, 2013, pp. 1-4.
Written Opinion issued in PCT/EP2013/062298,WO2013/186320, Feb. 8, 2013, pp. 1-13.
Hacker, "Aromatic 2-(Thio)ureidocarboxylic Acids as New Family of Modulators of Multidrug Resistance-Associated Protein 1: Synthesis, Biological Evaluation, and Structure-Activity Relationships," Journal of Medicinal Chemistry, 2009, vol. 52, No. 15, pp. 4587-4593.
Office Action issued in Chinese Patent Application Serial No. 2011800243402, Dec. 8, 2014, pp. 1-13, translation included.
International Preliminary Report on Patentability issued in PCT/EP2012/061346, WO2012/172015, Jun. 3, 1014, pp. 1-29.
International Preliminary Report on Patentability issued in PCT/EP2012/061346, WO2012/172015, Oct. 9, 2013, pp. 1-8.
International Search Report issued in PCT/EP2012/061346, WO2012/172015, Aug. 1, 2012, pp. 1-9.
Saksena, Anil K.; Girijavallabhan, Viyyoor M.; Lovey, Raymond G.; Pike, Russell E.; Wang, Haiyan; Ganguly, Ashit K.; Morgan, Brian; Zaks, Alesey; Puar, Mohinder S., Highly stereoselective access to novel 2,2,4-trisubstituted tetrahydrofurans by halocyclization: practical chemoenzymic synthesis of SCH 51048, a broad-spectrum orally active antifungal agent, Tetrahedron Letters, 1995, 36(11), pp. 1787-1790.
Konosu, Toshiyuki; Tajima, Yawara; Miyaoka, Takeo; Oida, Sadao, Concise synthesis of optically active oxirane precursors for the preparation of triazole antifungals using the Friedel-Crafts reaction of (S)-2-tosyloxypropionyl chloride, Tetrahedron Letters, 1991, 32(51), pp. 7545-7548.
Japanese Office Action issued Mar. 3, 2015, in Japanese Patent Application No. 2013-510614, pp. 1-6.

* cited by examiner

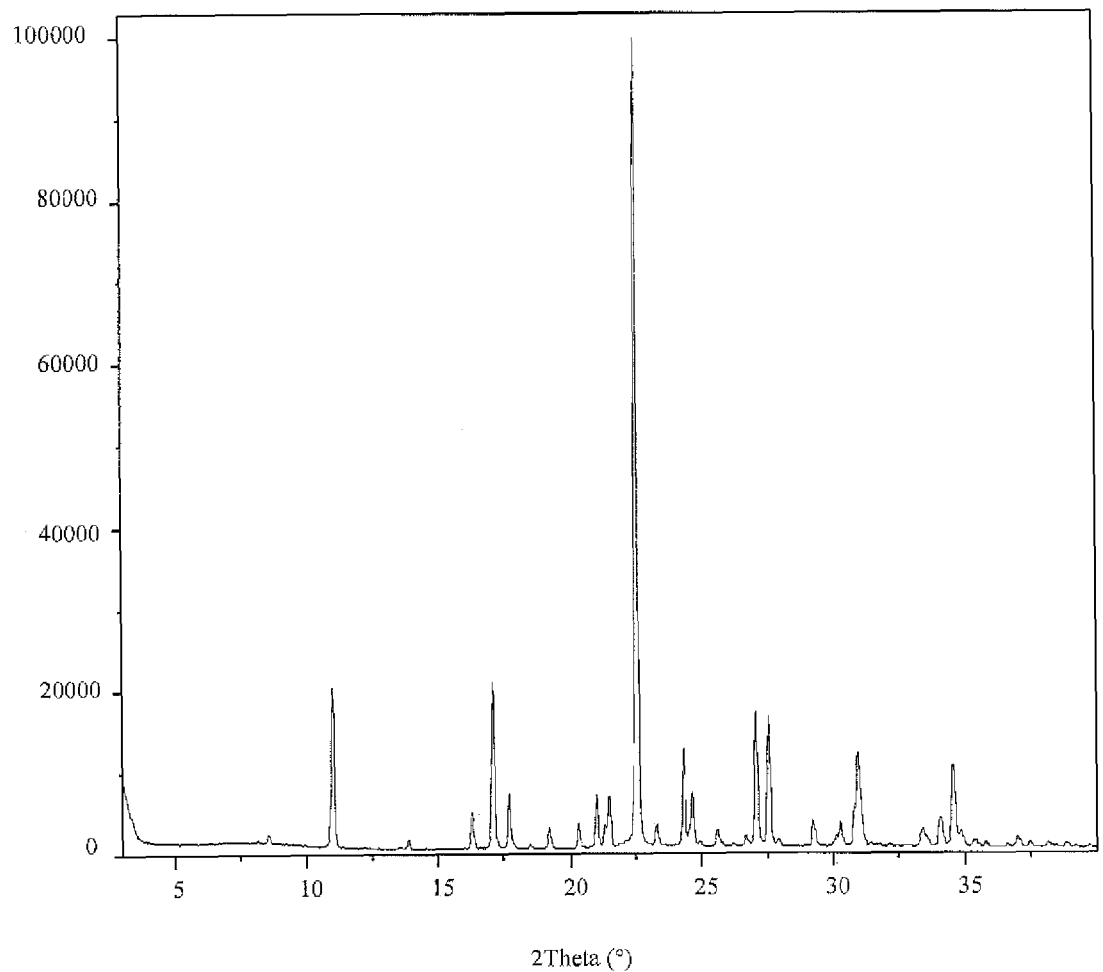

PURIFICATION OF POSACONAZOLE AND OF POSACONAZOLE INTERMEDIATES

The present invention relates to the purification of chiral compounds, in particular to the purification of a chiral compound which may be used as intermediate for the preparation of antifungal agents, preferably posaconazole.

BACKGROUND PRIOR ART

Posaconazole (CAS Registry Number 171228-49-2; CAS Name: 2,5-anhydro-1,3,4-trideoxy-2-C-(2,4-difluorophenyl)-4-[[4-[4-[4-[1-[(1S,2S)-1-ethyl-2-hydroxypropyl]-1,5-dihydro-5-oxo-4H-1,2,4-triazol-4-yl]phenyl]-1-piperazinyl]phenoxy]methyl]-1-(1H-1,2,4-triazol-1-yl)-D-threo-pentitol) is a triazole antifungal drug represented by the structure:

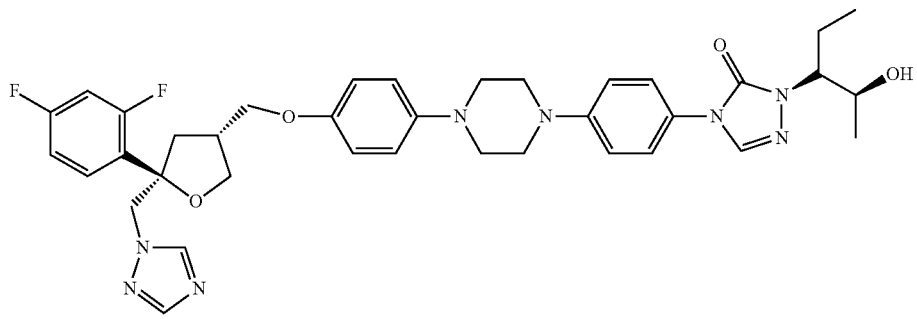

Posaconazole is used, for example, to prevent and/or treat invasive fungal infections caused by *Candida* species, *Mucor* species, *Aspergillus* species, *Fusarium* species, or *Coccidioides* species in immunocompromised patients and/or in patients where the disease is refractory to other antifungal agents such as amphothericin B, fluconazole, or itraconazole, and/or in patients who do not tolerate these antifungal agents.

One of the important intermediates for the preparation of posaconazole is the compound of formula (II)

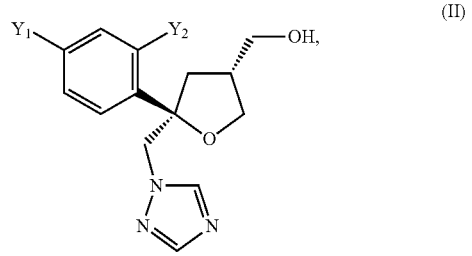

wherein both residues $Y_1$ and $Y_2$ are F. In a conceivable synthetic approach towards the compound of formula (II), the quaternary stereo center is generated by an iodo-cyclization, giving the required tetrahydrofuran as a diastereomeric mixture. In this mixture, the molar ratio of cis-isomer relative to the trans-isomer (cis:trans) is in the range of from 85:15 to 95:5, typically about 9:1. However, only the cis-isomer is desired to be transformed to posaconazole. Consequently, an enrichment of the desired cis-isomer or a suitable salt thereof is necessary.

According to the prior art, the diastereomeric mixture comprising, in a solvent, the cis-isomer of formula (II) and the trans-isomer of formula (III)

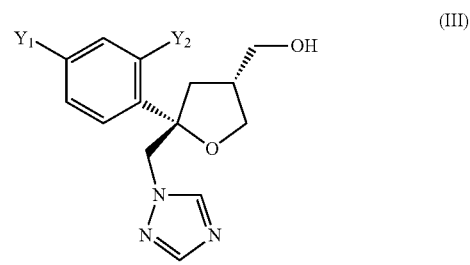

was converted, in a first step, to a diastereomeric mixture of the respective tosylates of compounds (II) and (III) exhibiting the same cis:trans ratio as the starting mixture, i.e. typically the 9:1 ratio. From this diastereomeric mixture, the cis-isomer had to be separated in a second step via tedious gradient column chromatography on silica gel using large volumes of a mixture of heptane and ethyl acetate. In the context, reference is made to U.S. Pat. No. 5,403,937, EP 0 736 030 A1, and WO 95/17407. However, column chromatography in general and the above-discussed column chromatography processes in particular are not suitable for industrial-scale processes.

Therefore, it was an object of the present invention to provide a new process for the separation of the cis-isomer according to formula (II).

Looking for such simplified and advantageous new process, it was found that most likely, making use of the known diastereomeric mixture of the tosylate of compounds (II) and (III) was not a promising starting point.

Therefore, it was another object of the present invention to provide a new intermediate containing suitable derivatives of the compounds of formula (II) and (III).

Surprisingly, it was found that above-discussed separation of the cis-isomer can be considerably simplified if, based on the diasteromeric mixture containing the compounds of formula (II) and (III), a specific salt is prepared. This specific salt was found to be the HCl salt of the compounds (II) and (III).

SUMMARY OF THE INVENTION

Therefore, the present invention relates to a process for the preparation of a hydrogen chloride (HCl) salt of a compound of formula (I)

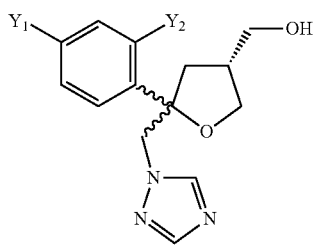

(I)

wherein Y₁ and Y₂ are independently F or Cl, preferably F, said compound of formula (I) containing the cis-isomer of formula (II) and the trans-isomer of formula (III)

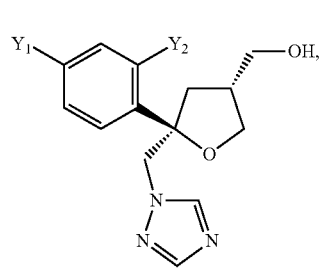

(II)

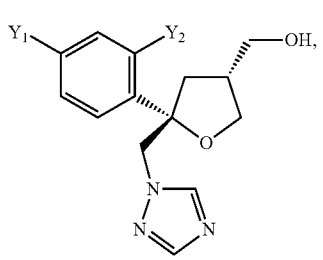

(III)

the process comprising (1) providing the compound of formula (I) comprised in a first suitable solvent;
(2) treating the compound of formula (I) comprised in the first suitable solvent with HCl comprised in a second suitable solvent to obtain the HCl salt of compound of formula (I).

Moreover, the present invention relates to the use of this process for the purification of a diasteromeric mixture of the cis-isomer of formula (II) and the trans-isomer of formula (III)

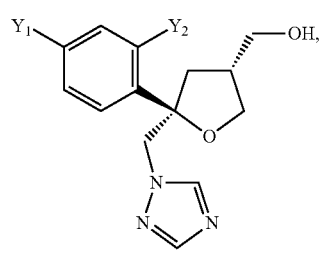

(II)

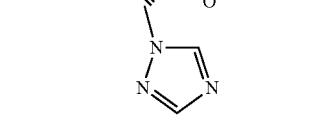

with regard to the cis-isomer.

Further, the present invention relates to a preferably crystalline hydrogen chloride (HCl) salt of a compound of formula (I)

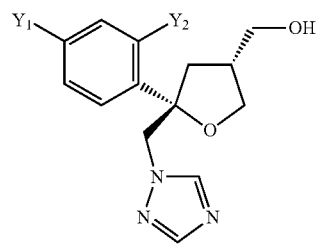

(III)

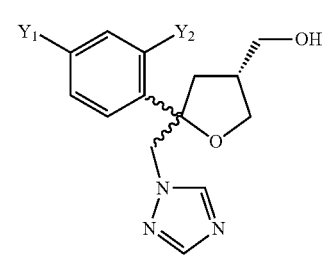

(I)

wherein Y₁ and Y₂ are independently F or Cl, preferably F, said compound of formula (I) containing the cis-isomer of formula (II) and the trans-isomer of formula (III)

(II)

(III)

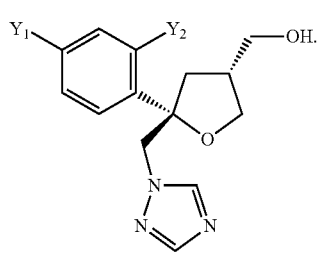

Yet further, the present invention relates to the use of said preferably crystalline HCl salt containing at least 99% of the HCl salt of the cis-isomer according to formula (II)

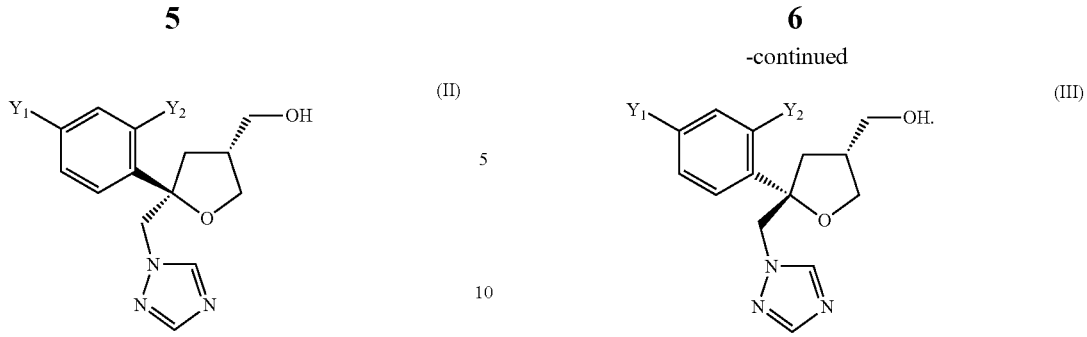

for the preparation of an antifungal agent, preferably posaconazole.

LIST OF FIGURES

FIG. 1 shows the X-ray powder diffraction pattern (XRD) of the compound of formula (I) as obtained according to Example 6 of the present invention. The cis:trans ratio, i.e. the ratio compound of formula (II):compound of formula (III) wherein $Y_1=Y_2=F$ is 99.2:0.8. In FIG. 1, on the x-axis, the position—expressed as 2 theta values in degrees—is shown, on the y-axis, the intensity—measured as counts per second (linear scale)—is shown.

DETAILED DESCRIPTION

According to the process of the present invention, a hydrogen chloride (HCl) salt of a compound of formula (I)

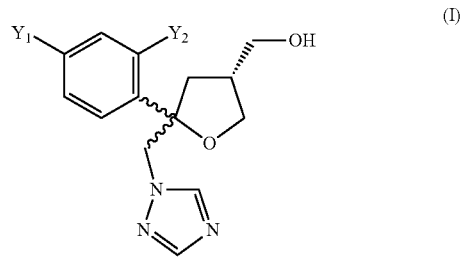

is prepared wherein $Y_1$ and $Y_2$ are independently F or Cl, preferably F, and wherein said compound of formula (I) contains the cis-isomer of formula (II) and the trans-isomer of formula (III)

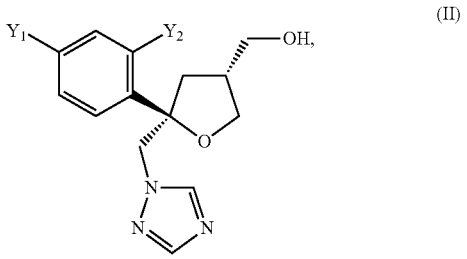

This process of the present invention comprises steps (1) and (2):

(1) providing the compound of formula (I) comprised in a first suitable solvent;

(2) treating the compound of formula (I) comprised in the first suitable solvent with HCl comprised in a second suitable solvent to obtain the HCl salt of compound of formula (I).

Generally, it is possible to prepare said HCl salt in step (2) starting from any mixtures containing the compounds of formula (II) and (III), with no specific restrictions as to the molar ratio of compound (II) relative to compound (III). According to a preferred embodiment of the present invention, the compound of formula (I) representing said mixture contains from 80 to 95%, preferably from 85 to 95% of the cis-isomer of formula (II) and from 20 to 5%, preferably from 15 to 5% of the trans-isomer of formula (III). Typically, therefore, the compound of formula (I) contains from 86 to 94% or from 87 to 93% or from 88 to 92% or from 89 to 91% of the cis-isomer of formula (II) and from 14 to 6% or from 13 to 7% or from 12 to 8% or from 11 to 9% of the trans-isomer of formula (III). Based on this preferred mixture, the preferred separation of the cis-isomer according to the present invention is performed.

Step (1)

As far as the compound of formula (I) provided in step (1) is concerned, no particular restrictions exist as far as the process of its preparation is concerned. Basically, one can provide the compound of formula (I) dissolved in a solvent wherein said solvent, in case it is not the first suitable solvent according to step (1) of the inventive process, can be suitably changed prior to step (1). According to a preferred embodiment of the present invention, the compound of formula (I) is provided by a method comprising the steps (i.1) to (vi.2) as described hereinunder. According to a further embodiment of the present invention, the compound of formula (I) is provided as an at least partially crystalline compound by a method, in addition to steps (i.1) to (vi.2) comprising a further step (vii) of at least partially crystallizing the compound of formula (I). The at least partially crystalline compound thus obtained is then admixed with the first suitable solvent.

Steps (i.1) to (vi.2)

Therefore, according to a preferred embodiment, the present invention relates to the process as described above, wherein in (1), the compound of formula (I) is provided by a method comprising (i.1) reacting a compound of formula (A)

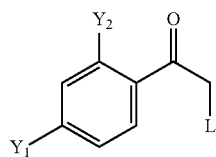

wherein L is a leaving group, preferably a halogen, more preferably Cl, in a solvent with a nucleophilic compound comprising a nucleophilic residue $R_aR_bR_cSi\text{—}CH_2$ wherein $R_a$, $R_b$ and $R_c$, are the same or different and selected from the group consisting of optionally suitably substituted alkyl and aryl residues, to obtain a reaction mixture containing as intermediate a beta-hydroxy silane of formula

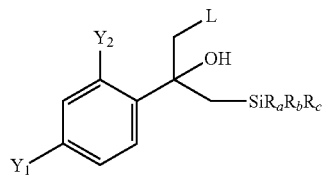

said reacting preferably being performed at a temperature in the range of from −50 to +20° C., more preferably from −30 to +10° C., more preferably from −15 to +5° C.;

(i.2) treating the resulting reaction mixture, preferably without change of solvent, with a reagent promoting elimination reaction to obtain a reaction mixture containing a compound of formula (B)

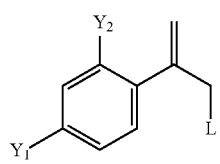

wherein treating is performed at a temperature in the range of from −20 to +70° C. and wherein said reagent is preferably an acid, preferably an inorganic acid, more preferably sulfuric acid, wherein, if sulfuric acid is used, the temperature at which said treating is performed is preferably in the range of from 40 to 50° C.;

(ii) reacting the compound of formula (B) with a malonic ester $R_1OOC\text{—}CH_2\text{—}COOR_2$ to obtain a compound of formula (C)

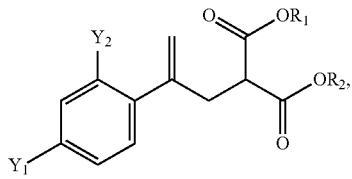

wherein $R_1$ and $R_2$ are independently an optionally suitably substituted alkyl group having from 1 to 5 carbon atoms, preferably ethyl, wherein, after (ii) and before (iii), the compound of formula (C) is optionally separated by extraction in a suitable solvent, preferably cyclohexane;

(iii) reducing the compound of formula (C) to obtain a compound of formula (D)

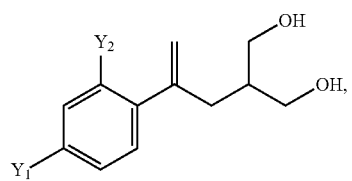

the reducing agent preferably being $LiBH_4$ which is used in an amount of at most 2 molar equivalents with respect to the compound of formula (C), said reduction preferably being carried out in a suitable solvent preferably comprising water, the solvent preferably being selected from the group consisting of water, alcohol, and a mixture of water and at least one alcohol, more preferably from the group consisting of water, methanol, ethanol, isopropanol, and a mixture of water and at least one of these alcohols, more preferably from the group consisting of water, ethanol, isopropanol, and a mixture of water and at least one of these alcohols, more preferably from the group consisting of water, isopropanol, and a mixture of water and isopropanol, the solvent most preferably being a mixture of water and isopropanol, wherein the solvent preferably comprises from 1 to 20 vol.-%, more preferably from 5 to 15 vol.-% of water;

(iv) acylating the compound of formula (D) with isobutyric anhydride to obtain a compound of formula (E)

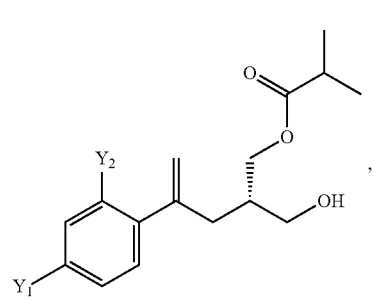

said acylation preferably being carried out in the presence of a suitable enzyme, preferably Novo SP 435 enzyme in a suitable solvent, preferably acetonitrile or toluene, more preferably toluene, wherein after (iv) and before (v), the compound of formula (E) is preferably at least partially crystallized;

(v) reacting the compound of formula (E) with a halogen Hal$_2$ selected from the group consisting of Cl$_2$, Br$_2$ and I$_2$, preferably I$_2$, in the presence of a base in a solvent to obtain a compound of formula (F)

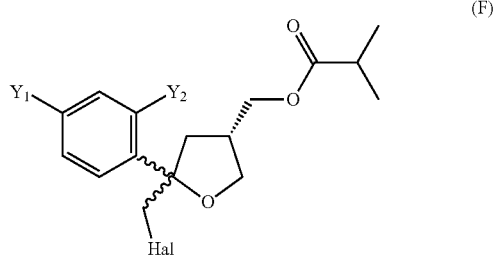

wherein preferably from 80 to 95%, more preferably from 85 to 95% of the molecules of compound (F) are present as cis-isomer of formula (Fa)

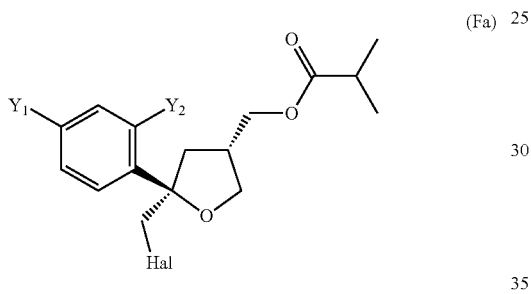

and preferably from 20 to 5%, more preferably from 15 to 5% of the molecules of compound (F) are present as trans-isomer of formula (Fb)

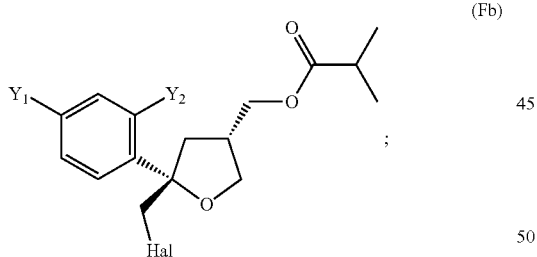

wherein the solvent is preferably ethyl acetate and wherein the base is preferably sodium hydrogencarbonate, and wherein the temperature at which the compound of formula (E) is reacted is preferably less than 0° C., more preferably not higher than −5° C. and even more preferably not higher than −10° C.;

(vi.1) heating the compound of formula (F) preferably at a temperature in the range of from +70 to +100° C., more preferably from +80 to +95° C., more preferably from +85 to +90° C., preferably in the absence of DMPU (1,3-dimethyl-3,4,5,6-tetrahydro-2(1H)-pyrimidinone), in a solvent, preferably a polar aprotic solvents, for example DMF (N,N-dimethylformamide) and DMSO, more preferably DMSO, with a 1,2,4-triazole alkali metal salt, preferably the sodium salt, and treating the resulting reaction mixture with a base suitable to promote saponification of the ester moiety such as alkali metal hydroxides, alkali metal bicarbonates, alkali metal carbonates, alkaline earth metal hydroxides, alkaline earth metal bicarbonates, and alkaline earth metal carbonates, preferably alkali metal bases, said base preferably being added in aqueous and/or alcoholic media, wherein suitable alcohols are alcohols containing 1 to 6, preferably 1 to 4, more preferably 1 to 3, most preferably 1 to 2 carbon atoms, said base even more preferably being sodium hydroxide, preferably employed as aqueous solution, in the presence of methanol, to obtain a compound of formula (I)

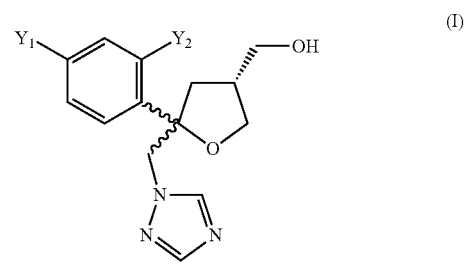

wherein preferably from 80 to 95%, more preferably from 85 to 95% of the molecules are present as cis-isomer of formula (II)

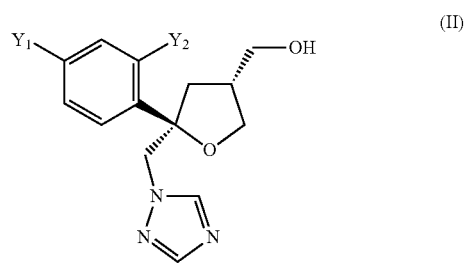

and preferably from 20 to 5%, more preferably from 15 to 5% of the molecules are present as trans-isomer of formula (III)

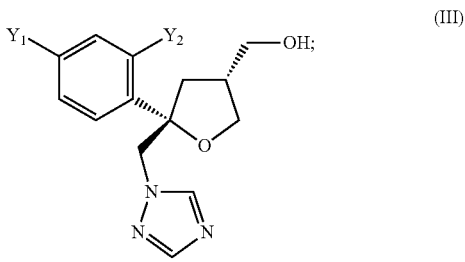

(vi.2) separating the compound of formula (I) from the reaction mixture obtained from (vi.1) by extraction in a suitable solvent, the solvent preferably being a polar water-immiscible solvent, more preferably an ester such as ethyl acetate or isopropyl acetate, an ether such as tetrahydrofuran or methyl tetrahydrofuran, a ketone such as methyl isobutyl ketone, a halogenated solvent such as dichloromethane, toluene, or a mixture of two or more of these solvents, more preferably an ester or an ether, more preferably an ether, and even more preferably methyl tetrahydrofuran.

Steps (i.1) to (vi.2) in Detail

Steps (i.1) and (i.2)

In step (i.1) of the inventive process, the compound of formula (A) comprises residues $Y_1$ and $Y_2$. According to the present invention, $Y_1$ and $Y_2$ are independently F or Cl. Thus, $Y_1$ may be F or Cl, and independently from the chemical nature of $Y_1$, $Y_2$ may be F or Cl. Preferably, both $Y_1$ and $Y_2$ are either F or Cl. More preferably, both $Y_1$ and $Y_2$ are F.

The term "leaving group L" as used in the context of step (i.1) of the present invention refers to any chemical moieties L which, under suitable reaction conditions, departs from compound (A) with a pair of electrons in a heterolytic bond cleavage. For this purpose, compound (A) as used in the present inventions may comprise any suitably leaving group L. Preferably, the leaving group L, after departing, is a neutral or an anionic moiety, more preferably an anionic moiety. Even more preferably, L is an halogen such as, for example, Cl, Br, I. According to an even more preferred embodiment of the present invention, L is Cl.

The nucleophilic compound with which compound (A) is reacted in step (i.1) comprises a nucleophilic residue $R_aR_bR_cSi$—$CH_2$. As to the chemical nature of this residue, there are no particular restrictions provided that the beta-hydroxy silane intermediate of formula

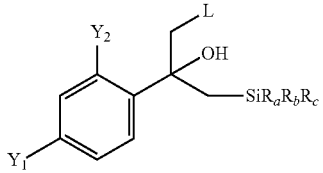

is obtained. The term "intermediate" as used in this context of the present invention generally refers to a beta-hydroxy silane which is comprised in the reaction mixture obtained in step (i.1) and which is formed from the reactants of step (i.1) and reacts further in (i.2). The term "intermediate" as used in this context does not exclude such beta-hydroxy silanes which can be isolated from the reaction mixture obtained in (i.1)

The nucleophilic compound employed in (i.1) can be any suitable compound comprising a nucleophilic residue $R_aR_bR_cSi$—$CH_2$ which, when reacted with compound (A), either directly or indirectly leads to the formation of the beta-hydroxy silane intermediate discussed above. $R_a$, $R_b$ and $R_c$ comprised in the nucleophilic compound are the same or different and selected from the group consisting of optionally suitably substituted alkyl and aryl residues. The term "optionally suitably substituted aryl residue" as used in the context of the present invention refers to aryl residues which have, for example, up to 6 or up to 12 carbon atoms. If such aryl residue is a substituted aryl residue, the number of carbon atoms refers to the number of carbon atoms of the corresponding unsubstituted aryl residue. The term "optionally suitably substituted alkyl residue" as used in the context of the present invention refers to alkyl residues which have, for example, 1 to 20, preferably 1 to 10 carbon atoms. If such alkyl residue is a substituted alkyl residue, the number of carbon atoms refers to the number of carbon atoms of the corresponding unsubstituted alkyl residue.

According to preferred embodiments of the present invention, $R_a$, $R_b$ and $R_c$ comprised in the nucleophilic compound are the same or different and selected from the group consisting of alkyl residues, more preferably non-substituted alkyl residues having from 1 to 6 carbon atoms, preferably from 1 to 4 carbon atoms such as methyl, ethyl, n-propyl, iso-propyl, n-butyl, iso-butyl, and tert-butyl, more preferably 1 or 2 carbon atoms, methyl or ethyl, with $R_a$, $R_b$ and $R_c$ in particular being methyl.

Preferably, the nucleophilic compound employed in (i.1) is a Grignard reagent. The term "Grignard reagent" as used in this context refers to any suitable nucleophilic organometallic reagent comprising the nucleophilic residue $R_aR_bR_cSi$—$CH_2$. Preferably the nucleophilic compound is a Grignard compound $R_aR_bR_cSi$—$CH_2MgX$ wherein X is a suitable anionic species which is preferably selected from the group consisting of Cl, Br, and I. More preferably, the Grignard compound is the compound $R_aR_bR_cSi$—$CH_2MgCl$.

As solvent which is employed in (i.1), any solvent or solvent mixture is conceivable, preferably a solvent or solvent mixture in which a Grignard reaction can be carried out. Conceivable solvents are, for example, ether compounds such as the commonly known diethyl ether and/or tetrahydrofuran (THF). Surprisingly, however, it was found in the context of the present invention that the solvents discussed in the background prior art in the context of the Peterson olefination, namely diethyl ether and THF, can be replaced by methyl-tert-butyl ether (MTBE). This solvent provides the major advantage that compared to compounds such as diethyl ether and THF, no peroxides are formed. Thus, the use of MTBE is especially suitable for industrial scale processes for which safety aspects are of utmost importance. Therefore, according to a particularly preferred embodiment, the solvent used in step (i.1) is MTBE.

Therefore, according to a preferred embodiment, the present invention relates to a process as defined above, wherein in (i.1), the compound of formula (A) is the compound (Aa)

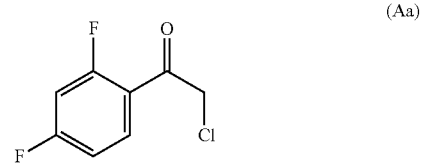 [SMILES: O=C(CCl)c1ccc(F)cc1F]

which is reacted in MTBE as solvent with the nucleophilic compound $(H_3C)_3Si$—$CH_2MgCl$ to obtain a reaction mixture containing as intermediate a beta-hydroxy silane of the formula:

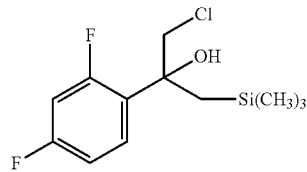

As to the temperatures at which the reaction in (i.1) is carried out, no particular restrictions exist provided a reaction mixture is obtained which allows for the reaction in (i.2). Preferably, reacting in (i.1) is performed at a temperature in the range of from −50 to +20° C., more preferably from −40 to +15° C., more preferably from −30 to +10° C., more preferably from −20 to +10° C., more preferably from −15 to +5° C. such as at a temperature in the range of from −15 to −10° C. or from −10 to −5° C. or from −5 to 0° C. or from 0 to +5° C.

As far as the general concept of the Peterson olefination is concerned, the literature teaches a two-step process wherein, after having carried out the Grignard reaction, a solvent exchange is performed. Reference is made to Tetrahedron Letters 32 (1991), pp. 7545-7548. Surprisingly, it was found that after step (i.1) of the present invention, no solvent exchange is necessary, and that the intermediate obtained from (i.1) can be treated with a suitable reagent which promotes elimination reaction in a considerably simplified process.

Therefore, according to the present invention, the reaction mixture resulting from (i.1) is treated in (i.2), preferably without change of solvent, with a reagent promoting elimination reaction to obtain a reaction mixture containing a compound of formula (B)

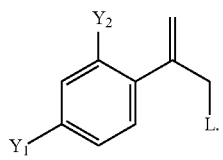

(B)

Since according to the literature, the second step of the Peterson olefination includes the use of $BF_3*Et_2O$ (boron trifluoride etherate), a further major advantage of the present invention is the fact that the use of potentially hazardous chemicals such as $BF_3$ etherate is completely avoided in this reaction stage. As discussed above, carrying out the inventive process without solvent exchange after (i.1) is particularly preferred if MTBE is used as solvent in (i.1).

As to the temperatures at which the reaction in (i.2) is carried out, no particular restrictions exist provided a reaction mixture is obtained containing the compound of formula (B). Preferably, treating in (i.2) is performed at a temperature in the range of from −20 to +70° C. Preferred temperature ranges are, for example, −20 to −10° C. or −10 to 0° C. or 0 to +10° C. or +10 to +20° C. or +20 to +30° C. or +30 to +40° C. or +40 to +50° C. or +50 to +60° C. or +60 to +70° C.

As to the reagent promoting elimination reaction employed in (i.2), no particular restrictions exist provided that the compound of formula (B) is obtained, preferably without solvent exchange after (i.1). Preferably, the reagent is an acid or a mixture of two or more acids. More preferably, the reagent is an inorganic acid or a mixture of two or more inorganic acids. Especially preferred is the use of sulfuric acid. Preferably, if sulfuric acid is used as reagent, the temperature at which (i.2) is performed is in the range of from +40 to +50° C.

Therefore, according to a preferred embodiment, the present invention relates to a process as defined above, wherein in (i.2), the reaction mixture resulting from (i.1) is treated without change of solvent with sulfuric acid promoting elimination reaction to obtain a reaction mixture containing, as compound of formula (B), the compound (Ba):

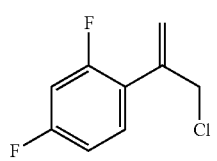

(Ba)

Thus, according to a still more preferred embodiment, the present invention relates to a process as defined above which comprises (i.1) reacting a compound of formula (Aa)

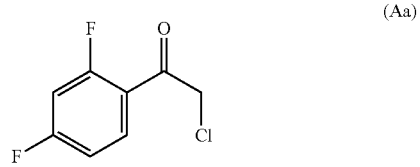 [SMILES: O=C(CCl)c1ccc(F)cc1F]

(Aa)

with $(H_3C)_3Si\text{—}CH_2MgCl$ in MTBE as solvent to obtain a reaction mixture containing as intermediate a beta-hydroxy slime of formula

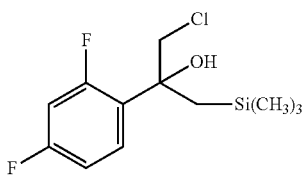

(i.2) treating the resulting reaction mixture without change of the solvent MTBE with sulfuric acid promoting elimination reaction to obtain a reaction mixture containing a compound of formula (Ba)

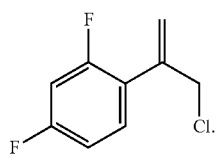

(Ba)

According to a still more preferred embodiment, the present invention relates to a process as defined above which comprises (i.1) reacting a compound of formula (Aa)

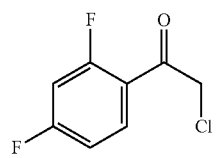

(Aa)

with $(H_3C)_3Si\text{—}CH_2MgCl$ in MTBE as solvent at a temperature in the range of from −15 to +5° C. to obtain a reaction mixture containing as intermediate a beta-hydroxy silane of formula

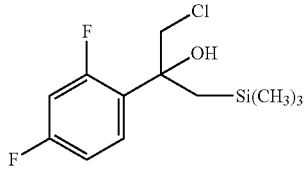

(i.2) treating the resulting reaction mixture without change of the solvent MTBE at a temperature in the range of from +40 to +50° C. with sulfuric acid promoting elimination reaction to obtain a reaction mixture containing a compound of formula (Ba)

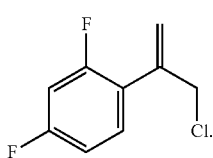
(Ba)

Steps (ii) to (vi.2)

From the compound contained in the reaction mixture obtained in (i.2) as discussed above, the compound of formula (I) is preferably prepared in steps (ii) to (vi.2). Thus, the process of the present invention further comprises (ii) reacting the compound of formula (B) with a malonic ester R$_1$OOC—CH$_2$—COOR$_2$ to obtain a compound of formula (C)

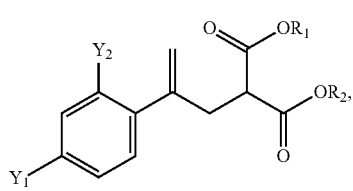
(C)

wherein R$_1$ and R$_2$ are independently an optionally suitably substituted alkyl group having from 1 to 5 carbon atoms;

(iii) reducing the compound of formula (C) to obtain a compound of formula (D)

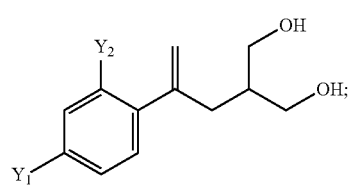
(D)

(iv) acylating the compound of formula (D) with isobutyric anhydride to obtain a compound of formula (E)

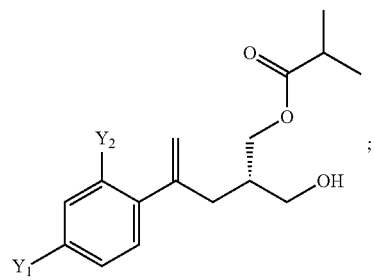
(E)

(v) reacting the compound of formula (E) with a halogen Hal$_2$ selected from the group consisting of Cl$_2$, Br$_2$ and I$_2$, preferably I$_2$, in the presence of a base in a solvent to obtain a compound of formula (F)

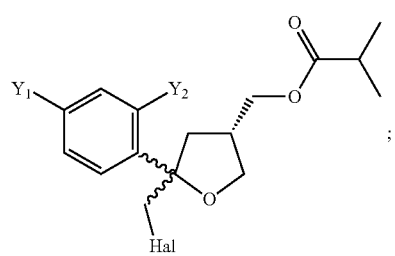
(F)

(vi.1) heating the compound of formula (F), preferably in the absence of DMPU (1,3-dimethyl-3,4,5,6-tetrahydro-2 (1H)-pyrimidinone), in a solvent, preferably DMSO (dimethyl sulfoxide), with a 1,2,4-triazole alkali metal salt, preferably the sodium salt, and treating the resulting reaction mixture with a base, to obtain a compound of formula (I)

(I)

(vi.2) separating the compound of formula (I) from the reaction mixture obtained from (vi.1) by extraction in a suitable solvent.

Step (ii)

According to step (ii) of the present invention, the compound of formula (B) is preferably reacted with a malonic ester R$_1$OOC—CH$_2$—COOR$_2$ wherein R$_1$ and R$_2$ are independently an optionally suitably substituted alkyl group having from 1 to 5 carbon atoms. The number of carbon atoms refers to the number of carbon atoms of the unsubstituted alkyl residue. Preferred alkyl groups R$_1$ and R$_2$ have 1 to 4 carbon atoms, such as methyl, ethyl, n-propyl, iso-propyl, n-butyl, iso-butyl, and tert-butyl. Even more preferably the alkyl groups R$_1$ and R$_2$ have 1 or 2 carbon atoms, such as methyl or ethyl, with ethyl being especially preferred. Even more preferably, the alkyl groups R$_1$ and R$_2$ are unsubstituted alkyl groups.

In step (ii), it is further preferred to react the malonic ester $R_1OOC—CH_2—COOR_2$ with compound (B) in the presence of a suitable strong base, preferably a strong alkali metal base allowing for the reaction of the respective anion $^-CH(COOR_1)(COOR_2)$ derived from the malonic ester $R_1OOC—CH_2—COOR_2$. As alkali metal, sodium is preferred. Suitable bases are, for example, NaH or NaOH, with NaOH being preferred. NaOH can be employed in every suitable form. According to a preferred embodiment, NaOH is employed as solid, such as, for examples, in the form of NaOH flakes. The solvent in which step (ii) is carried out can be chosen according to, for example, the specific chemical nature of the strong base as discussed above. Conceivable solvents are, for example, THF, DMSO or the like. According to present invention, DMSO is preferred. The temperatures at which the reaction in step (ii) is carried out can be chosen in accordance with the solvent and the base. Preferred temperatures are in the range of from 0 to 35° C., more preferably from 25 to 30° C.

The product of the reaction in (ii), the compound of formula (C)

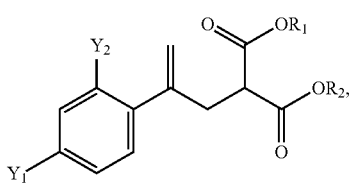

(C)

is preferably suitably separated from the reaction mixture obtained in (ii). According to a preferred embodiment, this separation includes a step wherein the compound (C) is separated by extraction in a suitable solvent. Among the suitable solvents, cyclohexane is preferred according to present invention.

The organic layer obtained from extraction can be washed in one or more steps. As washing agents, water and aqueous basic solutions such as, for example, aqueous solutions of alkali metal bases such as alkali metal hydroxide, preferably sodium hydroxide, are to be mentioned.

Step (iii)

According to a further preferred embodiment of the present invention, the compound of formula (C) obtained from step (ii) is suitably reduced wherefrom a compound of formula (D) is obtained:

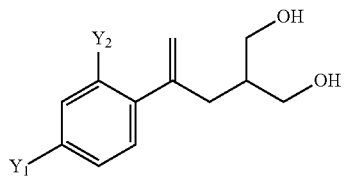

(D)

Reducing in step (iii) can be carried out according to any suitable method involving any suitable reducing agent. According to the present invention, the use of a hydride reducing agent is preferred. Such hydride reducing agents are, for example, sodium borohydride ($NaBH_4$), lithium borohydride ($LiBH_4$), lithium aluminium hydride (LIMBO, diisobutylaluminium hydride (DIBAL) or lithium triethylborohydride ($LiEt_3BH$). According to a preferred embodiment of the present invention, $LiBH_4$ is employed as reducing agent in step (iii).

According to the prior art, at least 3 molar equivalents of $LiBH_4$ have to be employed with regard to the compound of formula (C). Reference is made to WO 94/25452, page 31, section "Preparation 5". Surprisingly, however, contrary to the teaching of the prior art, the reducing agent $LiBH_4$ can be employed in a much lower excess with regard to the malonic ester compound (C). The improved process of the present invention uses at most 2 molar equivalents of $LiBH_4$ with regard to the compound of formula (C), which means that compared to the prior art, at least 33% of reducing agent can be saved. Thus, in particular for an industrial scale process, the present invention provides economical and ecological advantages. Thus, the present invention relates a process as defined above, wherein $LiBH_4$ is used as reducing agent which is preferably used in an amount of at most 2 molar equivalents with respect to compound (C).

As to the solvent in which the reaction of step (iii) is carried out, no particular restrictions exist provided that the compound of formula (D) is obtained. Preferred solvents are selected from the group consisting of water, alcohol, and a mixture of water and at least one alcohol. Preferred alcohols are methanol, ethanol, and isopropanol. Therefore, the solvent is preferably selected from the group consisting of water, methanol, ethanol, isopropanol, and a mixture of water and at least one of these alcohols, more preferably from the group consisting of water, ethanol, isopropanol, and a mixture of water and at least one of these alcohols, more preferably from the group consisting of water, isopropanol, and a mixture of water and isopropanol.

Surprisingly, it was found that in particular for the most preferred reducing agent used in step (iii), $LiBH_4$, a mixture of water and isopropanol is the most advantageous solvent. Contrary to the fact that water is known as decomposing hydride reducing agent, the presence of water was found to be advantageous in step (iii) of the inventive process. Without wanting to be bound to any theory, it is believed that this could be due to the fact that a certain amount of water improves the solubility of the reagent $LiBH_4$, and/or of its precursors $NaBH_4$ and LiCl, and thus enhances the reaction rate, and thus in turn overcompensates the decomposition of the reducing agent.

Therefore, according to still further embodiments, the solvent used in step (iii) comprises water, wherein the solvent preferably comprises from 1 to 20 vol.-%, more preferably from 5 to 15 vol.-% of water.

The temperatures at which the reaction in step (iii) is carried out can be chosen in accordance with the solvent and the reducing agent. Preferred temperatures are in the range of from 0 to 40° C., more preferably from 20 to 35° C., more preferably from 25 to 30° C.

The product of the reduction in (iii), the compound of formula (D), is preferably suitably separated from the reaction mixture obtained in (iii). According to a preferred embodiment, this separation includes a step wherein the compound (D) is separated by extraction in a suitable solvent. Among the suitable solvents, toluene is preferred according to the present invention.

Step (iv)

According to step (iv) of the present invention, the compound of formula (D) is preferably acylated with isobutyric anhydride to obtain a compound of formula (E)

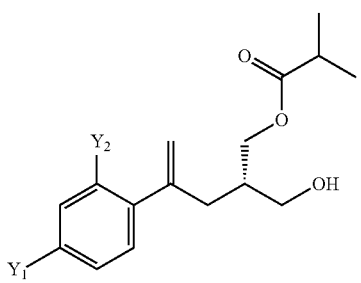

(E)

More preferably acylation in (iv) is carried out in the presence of a suitable enzyme, preferably Novo SP 435 enzyme in a suitable solvent, preferably acetonitrile or toluene, more preferably toluene, e.g. analogously to the method described in WO 97/22710. The choice of toluene as solvent is also beneficial in extractive work up as no additional solvent is required. In case of acetonitrile as solvent it is required to use an additional immiscible solvent for extractive work up.

The temperatures at which the acylation in step (iv) is carried out can be chosen in accordance with the solvent, the acylation agent and the enzyme. Preferred temperatures are in the range of from −20 to −5° C., more preferably from −15 to −10° C., more preferably from 25 to 30° C.

The obtained reaction mixture is preferably further treated with a suitable base such as, for example, sodium hydrogencarbonate.

According to an especially preferred embodiment of the present invention, the compound of formula (E) is suitably crystallized from the reaction mixture. Therefore, the present invention also relates to a process as defined above wherein after (iv) and before (v), the compound of formula (E) is at least partially crystallized. Crystallization can be carried out according to any conceivable method. According to a preferred embodiment, the compound if formula (E) is crystallized from n-heptane.

Step (v)

According to step (v) of the present invention, the compound of formula (E) is preferably reacted with a halogen $Hal_2$ selected from the group consisting of $Cl_2$, $Br_2$ and $I_2$, preferably $I_2$, in the presence of a base in a solvent to obtain a compound of formula (Fa)

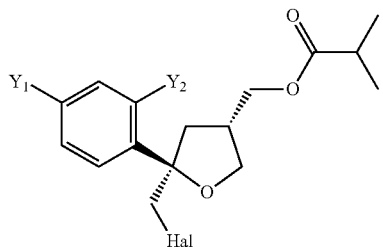

(Fa)

Generally, it is possible to carry out the reaction in step (v) in the presence of base such as pyridine and in a suitable solvent such as acetonitrile, THF, EtOAc (ethyl acetate) or $CH_2Cl_2$ (dichloromethane, DCM) at a temperature in the range of from −20 to +30° C. Reference is made to WO 94/25452 A1, pages 16 and 35. However, in the context of the present invention, it was found that the reaction is suitably carried out in ethyl acetate as solvent wherein as base, sodium hydrogencarbonate is employed. Thus, the present invention provides a process which allows for replacing the non-harmless base pyridine. Further, it was found that the temperature for carrying out the reaction is preferably less than 0° C., more preferably not higher than −5° C. and even more preferably not higher than −10° C.

After the reaction, the organic layer, optionally after suitable quenching, may be optionally washed at least once. Quenching may be done e.g. using a 10% (w/v) aqueous solution of sodium sulphite.

According to a particularly preferred embodiment, the present invention relates to a process as defined above wherein the compound of formula (Fa), the cis-isomer, is obtained in step (v) together with the compound of formula (Fb), the respective trans-isomer

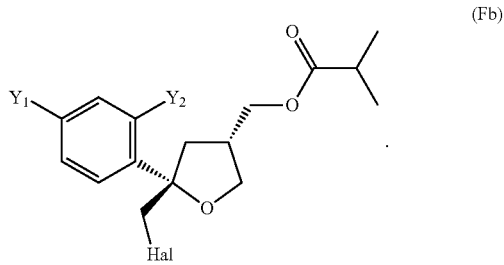

(Fb)

This mixture of the compounds of formula (Fa) and (Fb) is referred to in the following as compound of formula (F)

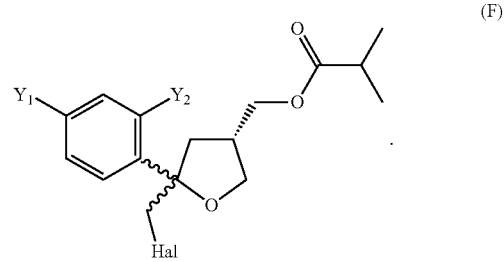

(F)

In said compound (F), according to the present invention, preferably from 80 to 95%, more preferably from 85 to 95% of the molecules are present as cis-isomer of formula (Fa) and preferably from 20 to 5%, more preferably from 15 to 5% of the molecules of compound (F) are present as trans-isomer of formula (Fb).

Therefore, the present invention also relates to the process as defined above, further comprising (v) reacting the compound of formula (E) with a halogen $Hal_1$ selected from the group consisting of $Cl_2$, $Br_2$ and $I_2$, preferably $I_2$, in the presence of a base in a solvent to obtain a compound of formula (F)

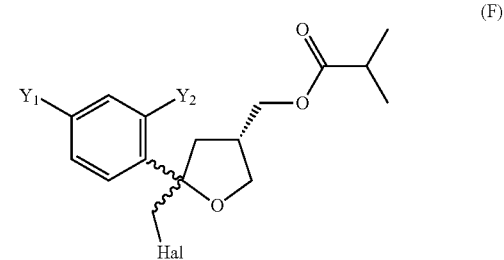

(F)

wherein preferably from 80 to 95%, more preferably from 85 to 95% of the molecules of compound (F) are present as cis-isomer of formula (Fa) and preferably from 20 to 5%, more preferably from 15 to 5% of the molecules of compound (F) are present as trans-isomer of formula (Fb).

Step (vi.1)

According to step (vi.1) of the present invention, the compound of formula (F), i.e. in particular the compound of formula (Fa) and the compound of formula (Fb), is preferably suitably heated in a suitable solvent with a suitable 1,2,4-triazole salt. Preferred 1,2,4-triazole salts are alkali metal salts, with the sodium salt being especially preferred. Preferred solvents are polar aprotic solvents, for example, DMF (N,N-dimethylformamide) and DMSO, with DMSO being preferred.

The temperature to which the reaction mixture in step (vi.1) is heated is preferably in the range of from +70 to +100° C., preferably from +80 to +95° C. and more preferably from +85 to +90° C.

As to such reactions with a triazole salt, WO 94/25452 teaches that such heating has to be carried out in the presence of 1,3-dimethyl-3,4,5,6-tetrahydro-2(1H)-pyrimidinone (DMPU). Reference is made to page 17, step (1), and page 39, step (b) of WO 94/25452. Surprisingly, contrary to the teaching in WO 94/25452, it was found that heating the compound of formula (F) in step (vi.1) can be performed in the absence of DPMU. Thus, according to the considerably improved process of the present invention, a simplified solvent system is provided which, according to a preferred embodiment, consists of DMSO only, i.e. of only one solvent compound contrary to the mandatory 2 compound system as taught in WO 94/25452.

The mixture obtained from heating is then preferably treated with a suitable base to promote saponification of the ester moiety. Such bases are, for example, alkali metal hydroxides, alkali metal bicarbonates, alkali metal carbonates, alkaline earth metal hydroxides, alkaline earth metal bicarbonates, and alkaline earth metal carbonates. The alkali metal bases are preferred. Preferably, the base is added in aqueous and/or alcoholic media. Suitable alcohols are alcohols containing 1 to 6, preferably 1 to 4, more preferably 1 to 3, most preferably 1 to 2 carbon atoms. According to the present invention, it was found that a preferred base is sodium hydroxide, preferably employed as aqueous solution, in the presence of methanol.

According to the present invention, in step (vi.1), the compound of formula (I)

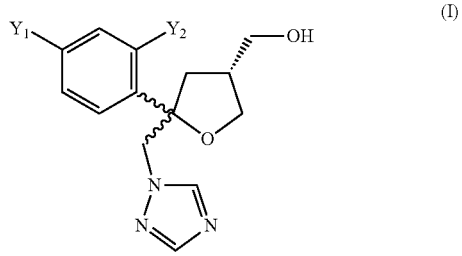

(I)

is obtained, wherein preferably from 80 to 95%, more preferably from 85 to 95% of the molecules are present as cis-isomer of formula (II)

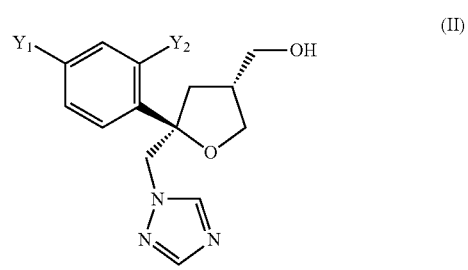

(II)

and preferably from 20 to 5%, more preferably from 15 to 5% of the molecules are present as trans-isomer of formula (III)

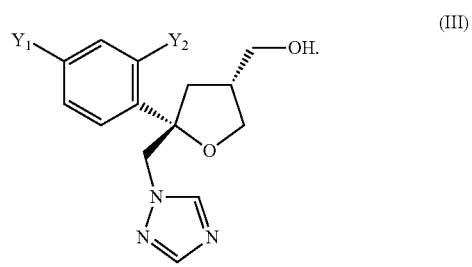

(III)

According to the prior art, it is necessary to separate the compound of formula (I) and thus of formula (II), after reaction steps corresponding to step (vi.1) of the present invention by chromatography. Reference is made to WO 94/25452, page 39, step (b). Thus, the prior art explicitly teaches that a costly and time-consuming purification has to be performed which renders the known process considerably detrimental concerning its industrial-scale application.

Contrary to the teaching of the prior art, it was found in the context of the present invention that no such separation by chromatography has to be carried out if the specific sequence of steps (vi.1) and extraction in (vi.2), optionally the crystallization in a step (vii), and the inventive salt formation in step (2) as described below is carried out. Thus, this modification represents a considerable improvement over the prior art processes.

Step (vi.2)

According to step (vi.2) of the present invention, the compound of formula (I)

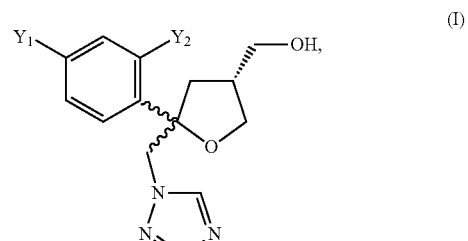

(I)

in particular the compound of formula (II)

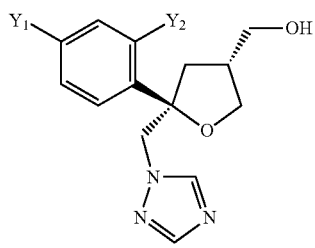

and the compound of formula (III)

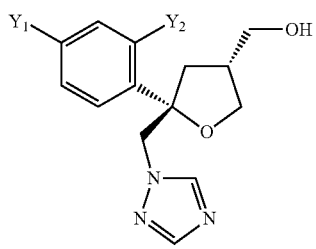

comprised in the mixture obtained from step (vi.1) is suitably separated, preferably by extraction into a suitable solvent.

Preferred solvents according to the present invention are polar water-immiscible solvents. More preferably, the solvent is an ester such as ethyl acetate or isopropyl acetate, an ether such as tetrahydrofuran or methyl tetrahydrofuran, a ketone such as methyl isobutyl ketone, a halogenated solvent such as dichloromethane, toluene, or a mixture of two or more of these solvents, more preferably an ester or an ether, more preferably an ether, and even more preferably methyl tetrahydrofuran.

Step (vii)

As mentioned above, the process of the present invention may further comprise a further step (vii) of at least partially crystallizing the compound of formula (I). The at least partially crystalline compound thus obtained is then admixed with the first suitable solvent.

Therefore, the present invention also relates to the process as described above, wherein in (1), the method according to which the compound of formula (I) is provided in (1) further comprises (vii) at least partially crystallizing the compound of formula (I), in particular the compound of formula (II) and the compound of formula (III), after (vi.2), wherein the compound of formula (I) is preferably crystallized from a solvent optionally by addition of a suitable antisolvent, wherein the solvent is preferably the solvent or solvent mixture employed in (vi.2) and wherein the antisolvent is preferably a saturated or unsaturated hydrocarbon such as cyclohexane, hexane, or heptane, or a mixture of two or more thereof.

After crystallization, the crystallized compound of (I), in particular the crystallized compound of formula (II) and the crystallized compound of formula (III), is preferably separated from the mother liquor, for example by suitable filtration, and preferably washed at least once with a suitable washing agent. Preferred washing agents are the solvent mixture used for the crystallization and the antisolvent discussed above. After such preferred separation, the crystallized compound of formula (I), in particular the crystallized compound of formula (II) and the crystallized compound of formula (III), is preferably dried under suitable drying conditions. Drying in vacuo is preferred wherein the temperatures are preferably in the range of from 20 to 50° C., more preferably from 30 to 45° C.

According to the process of the present invention, and as described above, the crystalline chiral compound of formula (II), the cis-isomer

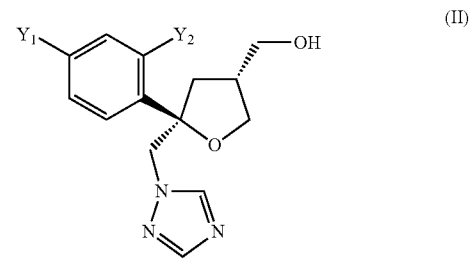

is obtained as mixture with its diasteromeric form, the crystalline compound of formula (III), namely the trans-isomer

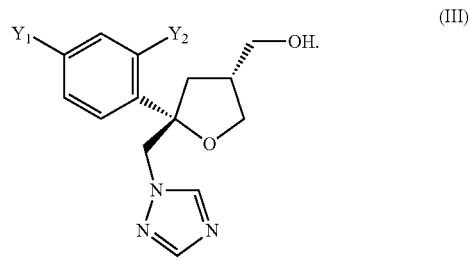

According to preferred process conditions of the process of the present invention, the crystallized compound of formula (I) obtained after step (vii),

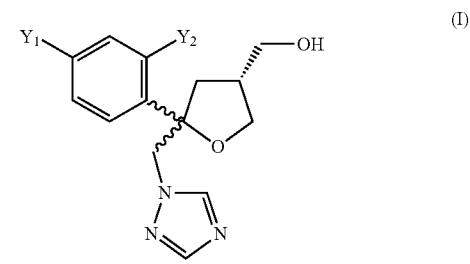

preferably contains from 80 to 95%, more preferably from 85 to 95% of the cis-isomer (II) and preferably from 20 to 5%, more preferably from 15 to 5% of the trans-isomer (III).

Further according to step (1) of the present invention, the compound of formula (I) is provided in a first suitable solvent prior to being treated with HCl which is comprised in a second suitable solvent.

Generally, there are no specific restrictions as to the chemical nature of the first suitable solvent provided that treatment with HCl comprised in the second suitable solvent allows for obtaining the HCl salt of the compound of formula (I). According to the present invention, a preferred solvent in which the compound of formula (I) is comprised according to step (1) is an organic solvent, preferably an alcohol and/or a precursor of an alcohol, an ether, a ketone, an ester, or a mixture of two or more thereof. The term "precursor of an alcohol" as used in this context of the present invention refers to a compound from which, under the process conditions in step (1) or steps (1) and (2), an alcohol is formed. By way of example, for illustrating the term "precursor of an alcohol", the cyclic ether compounds dioxane, methyl tetrahydrofuran or tetrahydrofuran shall be mentioned which, under acidic conditions, are at least partially present as the respective open-chain alcohols.

According to still further embodiments of the present invention, the first suitable solvent in which the compound of formula (I) is comprised is selected from the group consisting of ethyl acetate, isopropyl acetate, diethyl ether, tetrahydrofuran (THF), methyl tetrahydrofuran, dioxane, methanol, n-propanol, 1-butanol, 2-butanol, 2-methyl-1-butanol, 3-methyl-1-butanol, acetone, 2-butanone, and methyl isobutyl ketone (MIBK), and wherein the second solvent is selected from the group consisting of dioxane, tetrahydrofuran (THF), diethyl ether, diisopropyl ether, methyl tert-butyl ether (MTBE), ethyl acetate, methanol, n-propanol, 1-butanol, 2-butanol, 2-methyl-1-butanol, 3-methyl-1-butanol, and toluene.

Generally, as first suitable solvent, also mixture of two or more of the respective solvents can be used. Generally, as second suitable solvent, also mixture of two or more of the respective solvents can be used.

Step (2)—Increasing the Purity with Regard to the Cis-Isomer

Surprisingly, it was found that specific combinations of a first suitable solvent and a second suitable solvent allow for increasing the ratio of cis-isomer (II) to trans-isomer (III) in steps (1) and (2), in particular if crystallization is performed after step (2). In particular for the case where the compound of formula (I) as provided in step (1) contains from 80 to 95%, preferably from 85 to 95% of the cis-isomer (II) and from 20 to 5%, preferably from 15 to 5% of the trans-isomer (III), this specific combination of solvents provides the possibility that by simple means of crystallization, said increase of the ratio of cis-isomer (II) to trans-isomer (III) can be achieved, without using the time-consuming and costly gradient column chromatography as described in the prior art. According to this specific embodiment of the present invention, the first and/or the second solvent comprise an alcohol and/or a precursor of an alcohol.

Therefore, the present invention also relates to the process as defined above, wherein the first and/or the second solvent comprise(s) an alcohol and/or a precursor of an alcohol.

Even more preferably, it was found that a particularly preferred embodiment is the combination of a first suitable solvent which is MIBK and a second suitable solvent which is THF. Further, it was found that yet another particularly preferred embodiment is wherein n-butanol is used as the first and second suitable solvent.

Generally, there are no specific restrictions as far as the temperatures are concerned under which treatment in step (2) is carried out. Depending on the boiling points of the solvents used, preferred temperatures are in the range of from 20 to 100° C., preferably from 40 to 80° C., more preferably from 55 to 65° C. The temperature of the mixture obtained from step (1) can be higher, lower, or essentially the same compared to the temperature under which step (2) is carried out. According to a preferred embodiment of the present invention, the mixture of compound of formula (I) and the first suitable solvent as provided in step (1) is heated to the temperature under which step (2) is carried out before the second suitable solvent comprising HCl is added. The term "the second suitable solvent comprising HCl" does not necessarily exclude such embodiment where at least a portion of HCl is added to the mixture as obtained from step (1) prior to adding the second suitable solvent, or embodiments where at least a portion of HCl is added to the mixture as obtained from step (1) after adding the second suitable solvent. According to a preferred embodiment of the present invention, HCl needed for the treatment in step (2) is essentially completely contained in the second suitable solvent and, thus, added to the mixture obtained from step (1) together with the second suitable solvent.

Generally, it is possible to employ HCl in any amounts provided that after step (2), in particular after crystallization after step (2), the ratio of cis-isomer (II) to trans-isomer (III) is increased compared to the respective ratio in the compound of formula (I) employed in step (1). According to preferred embodiments of the present invention, HCl comprised in the second solvent is employed in step (2) relative to the compound of formula (I) in a molar ratio HCl:(I) in the range of from 1.0:1 to 2.0:1, preferably from 1.1:1 to 1.8:1, more preferably from 1.2:1 to 1.7:1, more preferably from 1.3:1 to 1.5:1.

As discussed above, HCl is comprised in the second solvent used in step (2) of the inventive process. Surprisingly, it was found that HCl cannot be substituted by other acids such as $H_2SO_4$, HBr, $HNO_3$, $H_3PO_4$, trifluoroacetic acid or other organic acids. Therefore, according to a conceivable embodiment of the present invention, step (2) is performed wherein the second solvent contains, as acidic component, only HCl.

As mentioned above, after step (2), the HCl salt of the compound of formula (I) is preferably at least partially crystallized. In this context, embodiments are included wherein said crystallization is at least partially achieved during step (2). Seeding can be performed for suitable initialization of the crystallization. However, in the context of the present invention, seeding is not necessary and crystallization without seeding is preferred.

Generally, the temperatures at which said crystallization is performed are adjusted to the solvents used. According to a preferred embodiment of the present invention, the temperature is in the range of from 20 to 100° C., preferably from 40 to 80° C., and more preferably from 55 to 65° C. Thereafter, it is preferred to cool the resulting mixture continuously to a preset temperature wherein cooling can be carried out continuously, or step-wise in two or more steps. According to an embodiment of the present invention, the preset temperature to which the mixture is ultimately cooled is in the range of from 0 to 30° C., preferably from 20 to 30° C.

After crystallization, the at least partially crystallized HCl salt of compound of formula (I) exhibiting an increased ratio of cis-isomer (II) to trans-isomer (III) is preferably separated from the mother liquor, for example by suitable filtration, and preferably washed at least once with a suitable washing agent. Preferred washing agent is, for example, one of the first suitable solvents as described above, with MIBK being especially preferred. Therefore, the present invention also relates to a process as defined above, which process further comprises (2a) separating the at least partially crystallized HCl salt of compound of formula (I), preferably by filtration, optionally followed by washing with a suitable solvent, preferably with MIBK.

After such preferred separation, the at least partially crystallized HCl salt of compound of formula (I) is preferably dried under suitable drying conditions. Drying in vacuo is preferred wherein the temperatures are preferably in the range of from 30 to 55° C., more preferably from 40 to 50° C.

As mentioned above, the compound of formula (I) employed as starting material in step (1) usually contains from 80 to 95%, preferably from 85 to 95% of the cis-isomer (II) and from 20 to 5%, preferably from 15 to 5% of the trans-isomer (III). If such compounds (I) are employed, the at least partially crystallized HCl salt of compound of formula (I) obtained from HCl treatment in step (2) and crystallization as defined above contains more than 95%, preferably at least 96% of the HCl salt of the cis-isomer of formula (II) and less than 5%, preferably at most 4% of the HCl salt of the trans-isomer of formula (III). Even more preferably, however, the at least partially crystallized HCl salt of compound of formula (I) contains at least 97%, preferably at least 98% and more preferably at least 99% of the HCl salt of the cis-isomer of formula (II) and at most 3%, preferably at most 2% and more preferably at most 1% of the HCl salt of the trans-isomer of formula (III).

Thus, compared to the prior art, the present invention provides a considerably simplified process of purifying a compound of formula (I) with respect to the cis-isomer of formula (II). In particular regarding the preferred use of such purified compound of formula (I) for the preparation of an antifungal agent, in particular posaconazole, this process improvement avoiding complicated purification of the prior art allows for a straightforward scale-up.

Step (3)—Further Increasing the Purity by Solid Extraction

In case the purity of the at least partially crystallized HCl salt of compound of formula (I) obtained from step (2) and subsequent crystallization with respect to the cis-isomer of formula (II) should not meet the requirements of a subsequent use, such as the use for the preparation of an antifungal agent, preferably a compound of formula (VIII)

Before the inventive stage of subjecting the at least partially crystallized HCl salt to solid extraction is discussed in detail, it is noted that generally, step (3) of the present invention can also be performed based on an at least partially crystalline HCl salt of compound of formula (I) whose purity with regard to the cis-isomer has not been increased in steps (1) and (2). Also this combination of an inventive preparation of an HCl salt of the compound of formula (I) and the inventive solid extraction allows for easily obtaining an HCl salt of compound of formula (I) with an increased purity with respect to the cis-isomer of formula (II).

In particular, this inventive combination of reaction steps allows for employing a starting material in step (1) which usually contains from 80 to 95%, preferably from 85 to 95% of the cis-isomer (II) and from 20 to 5%, preferably from 15 to 5% of the trans-isomer (III). If such compounds (I) are employed, and if in steps (1) and (2) no increase in the purification with respect to the at least partially crystallized HCl salt of compound of formula (I) is achieved, the at least partially crystallized HCl salt of compound of formula (I) obtained from HCl treatment in step (2) and crystallization as defined above contains from 80 to 95%, preferably from 85 to 95% of the HCl salt of cis-isomer (II) and from 20 to 5%, preferably from 15 to 5% of the HCl salt of trans-isomer (III). After the inventive solid extraction in step (3), the at least partially crystallized HCl salt of compound of formula (I) obtained from (3) contains at least 97%, preferably at least 98% and more preferably at least 99% of the HCl salt of the cis-isomer of formula (II) and at most 3%, preferably at most 2% and more preferably at most 1% of the HCl salt of the trans-isomer of formula (III).

If, after step (3), the purity of the at least partially crystallized HCl salt of compound of formula (I) obtained from step

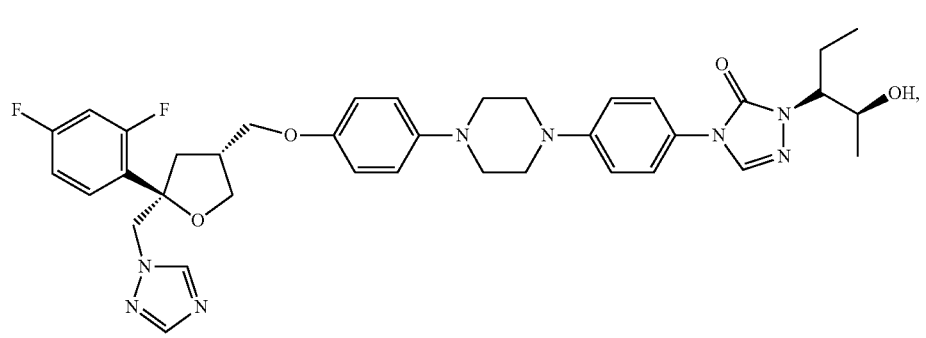

(VIII)

the present invention provides a further inventive step of increasing said purity of compound of formula (I). According to this embodiment of the present invention, the at least partially crystallized HCl salt of compound of formula (I) is further subjected to at least one suitable solid extraction stage wherefrom the HCl salt of compound of formula (I) with a further increased content with respect to the cis-isomer of formula (II) and a further decreased content with respect to the trans-isomer of formula (III) is obtained. Therefore, the present invention also relates to the process as defined above, further comprising (3) subjecting the at least partially crystallized HCl salt of compound of formula (I) to solid extraction in a suitable solvent, preferably comprising MIBK, to obtain the HCl salt of compound of formula (I), thereby increasing the content with regard to the HCl salt of the cis-isomer of formula (II).

(3) and subsequent isolation with respect to the cis-isomer of formula (II) should not meet the requirements of a subsequent use, such as the use for the preparation of an antifungal agent, preferably a compound of formula (VIII), it is generally possible to perform one or more additional solid extraction steps according to step (3).

Step (2) With No or Essentially No Increase in the Purity with Respect to (II)

If in steps (1) and (2), no or essentially no increase in the purity with respect to the cis-isomer (II) shall be achieved, there are no particular restrictions as far as the solvents used in step (1) and step (2) are concerned. In particular, it was found that contrary to the inventive embodiment according to which the cis:trans ratio is increased, it is not necessary for the first and/or the second solvent used in steps (1) and (2) to comprise an alcohol or a precursor of an alcohol. As to conceivable and preferred solvents other than alcohols or precursors of alcohols to be used in steps (1) and (2), reference is made to the respective discussion above.

According to a preferred embodiment of the present invention wherein no or essentially no increase in the purity with respect to the cis-isomer (II) shall be achieved in step (2), the compound of formula (I) is provided in step (1) in acetone as first suitable solvent. If the compound of formula (I) is prepared according to a method from which the compound is obtained in a solvent different from acetone, a suitable solvent exchange is preferred. As described above, the compound of formula (I) is preferably provided by a process comprising the steps (i.1) to (vi.2), more preferably without crystallization in step (vii), wherein according to a still further preferred embodiment, the compound of formula (I) is obtained in methyl tetrahydrofuran as solvent. Thus, it is preferred to suitably exchange methyl tetrahydrofuran by acetone prior to subjecting the compound of formula (I) to step (2) of the present invention.

Generally, there are no specific restrictions as far as the temperatures are concerned under which treatment in step (2) is carried out if no increase in the purity with regard to the cis-isomer shall be achieved. Depending on the boiling points of the solvents used, preferred temperatures are in range of from 0 to 100° C. The temperature of the mixture obtained from step (1) can be higher, lower, or essentially the same compared to the temperature under which step (2) is carried out. According to a preferred embodiment of the present invention, the mixture of compound of formula (I) and the first suitable solvent as provided in step (1) is heated to the temperature under which step (2) is carried out before the second suitable solvent comprising HCl is added. The term "the second suitable solvent comprising HCl" does not necessarily exclude such embodiment where at least a portion of HCl is added to the mixture as obtained from step (1) prior to adding the second suitable solvent, or embodiments where at least a portion of HCl is added to the mixture as obtained from step (1) after adding the second suitable solvent. According to a preferred embodiment of the present invention, HCl needed for the treatment in step (2) is essentially completely contained in the second suitable solvent and, thus, added to the mixture obtained from step (1) together with the second suitable solvent.

Generally, it is possible to employ HCl in any amounts. According to preferred embodiments of the present invention, HCl comprised in the second solvent is employed in step (2) relative to the compound of formula (I) in a molar ratio HCl:(I) in the range of from 1.0:1 to 3.0:1, preferably from 1.5:1 to 2.5:1, more preferably from 2.0:1 to 2.2:1.

As already discussed above, HCl is comprised in the second solvent used in step (2) of the inventive process. Surprisingly, it was found that HCl cannot be substituted by other acids such as $H_2SO_4$, HBr, $HNO_3$, $H_3PO_4$, trifluoroacetic acid or other organic acids. Therefore, according to a conceivable embodiment of the present invention, step (2) is performed wherein the second solvent contains, as acidic component, only HCl.

As mentioned above, after step (2), the HCl salt of the compound of formula (I) is preferably at least partially crystallized. In this context, embodiments are included wherein said crystallization is at least partially achieved during step (2). Seeding can be performed for suitable initialization of the crystallization. However, in the context of the present invention, seeding is not necessary and crystallization without seeding is preferred.

Generally, the temperatures at which said crystallization is performed are adjusted to the solvents used. According to a preferred embodiment of the present invention, the temperature is in the range of from 20 to 100° C., preferably from 40 to 80° C., and more preferably from 55 to 65° C. Thereafter, it is preferred to cool the resulting mixture to a preset temperature wherein cooling can be carried out continuously, or step-wise in two or more steps. According to an embodiment of the present invention, the preset temperature to which the mixture is ultimately cooled is in the range of from 0 to 30° C., preferably from 20 to 30° C.

After crystallization, the at least partially crystallized HCl salt of compound of formula (I) exhibiting the same or essentially the same ratio of cis-isomer (II) to trans-isomer (III) as the starting material, i.e. wherein the at least partially crystallized HCl salt contains from 80 to 95%, preferably from 85 to 95% of the HCl salt of the cis-isomer of formula (II) and from 20 to 5%, preferably from 15 to 5% of the HCl salt of the trans-isomer of formula (III), is preferably separated from the mother liquor, for example by suitable filtration, and preferably washed at least once with a suitable washing agent. Preferred washing agent is, for example, one of the solvents as described above, with methyl tert-butyl ether (MTBE), acetone or methyl isobutyl ketone (MIBK) being preferred and MTBE being especially preferred. Therefore, the present invention also relates to a process as defined above, which process further comprises (2b) separating the at least partially crystallized HCl salt of compound of formula (I), preferably by filtration, optionally followed by washing with a suitable solvent, preferably with methyl tert-butyl ether (MTBE), acetone or methyl isobutyl ketone (MIBK), more preferably with MTBE.

After such preferred separation, the at least partially crystallized HCl salt of compound of formula (I) is preferably dried under suitable drying conditions. Drying in vacuo is preferred wherein the temperatures are preferably in the range of from 30 to 55° C., more preferably from 40 to 50° C.

Step (3) in Detail

As mentioned above, step (3) of subjecting the at least partially crystallized HCl salt of the compound of formula (I) to solid extraction can be performed at least once if in the inventive process, the cis:trans ratio is increased in steps (1) and (2) and wherein this increased purity with respect to the cis-isomer should not meet specific requirements for a subsequent use of the compound of formula (I). Usually, if in steps (1) and (2) the cis:trans ratio is increased to a value of at least 97:3, preferably at least 98:2, more preferably at least 98.5:1.5 and even more preferably at least 99:1, it will not be necessary in most cases to perform one or more additional steps (3). If after steps (1) and (2), no increase in the cis:trans ratio is achieved or shall be achieved, or if the cis:trans ratio is increased to a value less than 97:3, it is a particularly preferred embodiment of the present invention to carry out at least one step (3) after steps (1) and (2).

As defined above, such step (3) comprises (3) subjecting the at least partially crystallized HCl salt of compound of formula (I) to solid extraction in a suitable solvent, preferably comprising MIBK, to obtain the HCl salt of compound of formula (I), thereby increasing the content with regard to the HCl salt of the cis-isomer of formula (II).

Generally, every suitable solvent or mixture of solvents can be used in step (3). According to an especially preferred embodiment, the solvent or solvent mixture employed in step (3) comprises MIBK. Therefore, in step (3), MIBK can be used as sole solvent, or as solvent in a suitable solvent mixture. While there are no specific restrictions as to other components of the solvent mixture provided the inventive solid extraction can be carried out, preferred solvent mixtures comprise, in addition to MIBK, at least one alcohol, or at least one precursor of an alcohol, or at least one alcohol and at least one precursor of an alcohol. As to the term "precursor of an alcohol", reference is made to the respective definition above. Even more preferably, the solvent mixture used in step (3) consists of MIBK and at least one alcohol, or at least one precursor of an alcohol, or at least one alcohol and at least one precursor of an alcohol. More preferably, solvent mixture used in step (3) consists of MIBK and at least one alcohol, even more preferably of MIBK and one alcohol. While there are no particular restrictions regarding this at least one alcohol, butanol, in particular n-butanol, is especially preferred.

As far as the molar ratio of MIBK relative to the alcohol, preferably butanol, even more preferably n-butanol is concerned, no specific restrictions exist. According to a preferred embodiment, the molar ratio of MIBK relative to the alcohol as employed in the solvent mixture used in step (3) is in the range of from 0.5:1 to 10:1, preferably from 0.75:1 to 5:1, and more preferably from 0.95:1 to 1.05:1.

Generally, the concentration of the HCl salt of compound of formula (I) in the solvent or solvent mixture used in step (3) can be adapted to the specific needs of the purification to be achieved. According to a preferred embodiment, the concentration of the HCl salt of compound of formula (I) is in the range of from 0.25 to 0.75, preferably from 0.55 to 0.65 mol/liter solvent or solvent mixture.

Generally, the temperatures at which said solid extraction is performed are adjusted to the solvent or solvent mixture used. According to a preferred embodiment of the present invention, the solid extraction in step (3) is carried out at a temperature in the range of from 20 to 100° C., preferably from 40 to 80° C., and more preferably from 55 to 65° C.

Thereafter, it is preferred to cool the resulting mixture to a preset temperature wherein cooling can be carried out continuously, or step-wise in two or more steps. According to an embodiment of the present invention, the preset temperature to which the mixture is ultimately cooled is in the range of from 0 to 30° C., preferably from 20 to 30° C.

The at least partially crystallized HCl salt of compound of formula (I) exhibiting an increased ratio of cis-isomer (II) to trans-isomer (III) is preferably isolated from the mixture obtained from solid extraction, for example by suitable filtration, and preferably washed at least once with a suitable washing agent. Preferred washing agent is, for example, one of the solvents as described above, with diethyl ether and/or methyl tert-butyl ether (MTBE) being especially preferred. Therefore, the present invention also relates to a process as defined above, which process further comprises (3a) isolating the at least partially crystallized HCl salt of compound of formula (I) from the mixture obtained from (3), preferably by filtration, optionally followed by washing with a suitable solvent, preferably with diethyl ether or methyl tert-butyl ether (MTBE).

After such preferred isolation, the at least partially crystallized HCl salt of compound of formula (I) is preferably dried under suitable drying conditions. Drying in vacuo is preferred wherein the temperatures are preferably in the range of from 30 to 55° C., more preferably from 40 to 50° C.

Prior to or after said drying step, the process according to the present invention may comprise at least one further step of subjecting the at least partially crystallized HCl salt as obtained from step (3) or step (3a) to solid extraction. As to the general and preferred conditions of such additional solid extraction or solid extractions, reference is made to the discussion of steps (3) and (3a) above. Therefore, the present invention also relates to the process as defined above comprising steps (3) and (3a), further comprising subjecting the HCl salt obtained from (3a) to solid extraction according to the above-defined process, preferably followed by isolating the thus obtained HCl salt according to the process as discussed in connection with step (3a).

As mentioned above, the HCl salt of compound of formula (I) employed as starting material in step (3) usually contains from 80 to less than 97%, preferably from 85 to less than 97% of the HCl salt of cis-isomer (II) and from 20 to more than 3%, preferably from 15 to more than 3% of the HCl salt of trans-isomer (III). If such compounds of formula (I) are employed, the at least partially crystallized HCl salt of compound of formula (I) obtained from solid extraction in step (3) and isolation as defined above contains at least 97%, preferably at least 98% and more preferably at least 99% of the HCl salt of the cis-isomer of formula (II) and at most 3%, preferably at most 2% and more preferably at most 1% of the HCl salt of the trans-isomer of formula (III).

Thus, it was found that either by a suitable combination of steps (1) and (2) with subsequent crystallization leading to a highly increased cis:trans ratio, optionally followed by at least one inventive solid extraction, or by a comparatively general combination of steps (1) and (2), especially preferably followed by at least one inventive solid extraction, it is possible to provide a considerably simplified process of purifying a compound of formula (I) with respect to the cis-isomer of formula (II), based on the key compound which is in both cases the HCl salt of compound of formula (I). In particular regarding to the preferred use of such purified compound of formula (I) for the preparation of an antifungal agent, in particular posaconazole, this process improvement avoiding complicated purification of the prior art allows for a straightforward scale-up.

Consequently, the present invention also relates to a preferably crystalline hydrogen chloride (HCl) salt of a compound of formula (I)

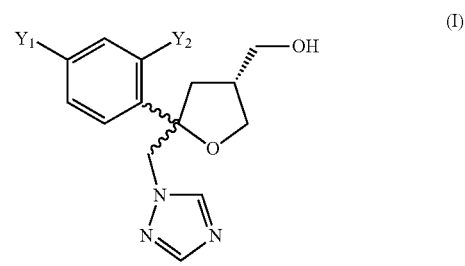

wherein $Y_1$ and $Y_2$ are independently F or Cl, preferably F, said compound of formula (I) containing the cis-isomer of formula (II) and the trans-isomer of formula (III)

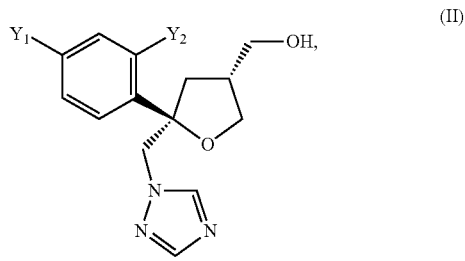

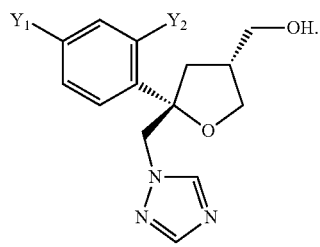

According to a preferred embodiment of the present invention, said preferably crystalline HCl salt contains at least 97%, preferably at least 98% and more preferably at least 99% of the HCl salt of the cis-isomer of formula (II) and at most 3%, preferably at most 2% and more preferably at most 1% of the HCl salt of the trans-isomer of formula (III).

Thus, in particular, the present invention relates to an at least partially crystalline, preferably a crystalline HCl salt of a compound of formula (I) with high purity with regard to the cis-isomer of formula (II), wherein $Y_1$ and $Y_2$ are F, and wherein said at least partially crystalline, preferably crystalline HCl salt contains at least 99% of the HCl salt of the cis-isomer of formula (II) and at most 1% of the trans-isomer of formula (III).

The crystalline HCl salt of the compound of formula (I) as herein described, wherein $Y_1$ and $Y_2$ are F, preferably exhibits the following X-ray diffraction pattern comprising at least the following reflections:

| Diffraction angle °2 Theta [Cu K(alpha 1)] | Relative Intensity (%) |
|---|---|
| 11.02 | 21 |
| 16.29 | 5 |
| 17.11 | 21 |
| 17.70 | 7 |
| 19.19 | 3 |
| 20.30 | 3 |
| 20.99 | 6 |
| 21.46 | 6 |
| 22.53 | 100 |
| 24.30 | 12 |
| 24.64 | 7 |
| 27.07 | 17 |
| 27.55 | 16 | wherein 100% relates to the intensity of the maximum peak in the X-ray diffraction pattern.

Additionally, the present invention relates to a preferably at least partially crystalline hydrogen chloride salt (HCl) salt of a compound of formula (I)

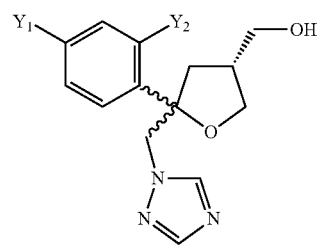

wherein $Y_1$ and $Y_2$ are independently F or Cl, preferably F, obtainable or obtained by a process as defined hereinabove.

As indicated above, such at least partially crystalline HCl salt of compound of formula (I) exhibiting said increased cis:trans ratios may be preferably used as starting materials for the preparation of an antifungal agent, preferably for the preparation of posaconazol, a compound of formula (VIII). In particular, such at least partially crystalline HCl salts of compound of formula (I) are especially suitable which contain at least 99% of the cis-isomer according to formula (II).

Therefore, the present invention also relates to the use of an at least partially crystalline HCl salt of the compound of formula (I) as defined above containing at least 99% of the HCl salt of the cis-isomer according to formula (II)

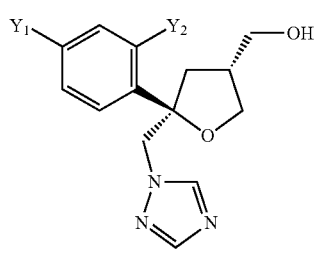

for the preparation of an antifungal agent, preferably, wherein both $Y_1$ and $Y_2$ are F, of a compound of formula (VIII)

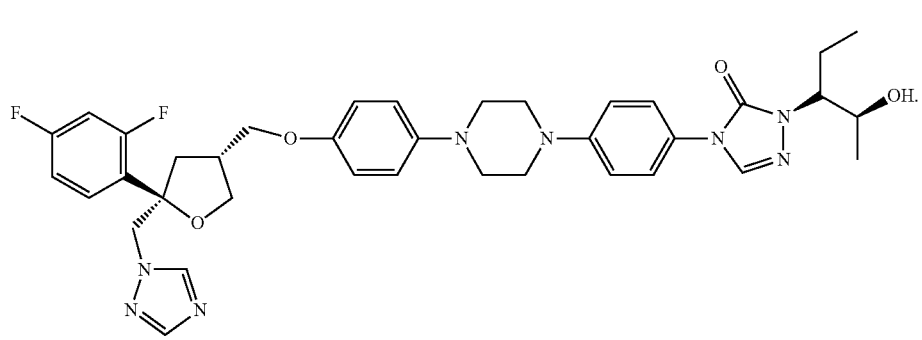

Also, the present invention relates to a method of using an at least partially crystalline HCl salt of the compound of formula (I) as defined above containing at least 99% of the HCl salt of the cis-isomer according to formula (II)

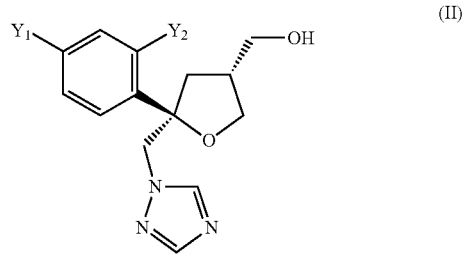

for the preparation of an antifungal agent, preferably, wherein both $Y_1$ and $Y_2$ are F, of a compound of formula (VIII)

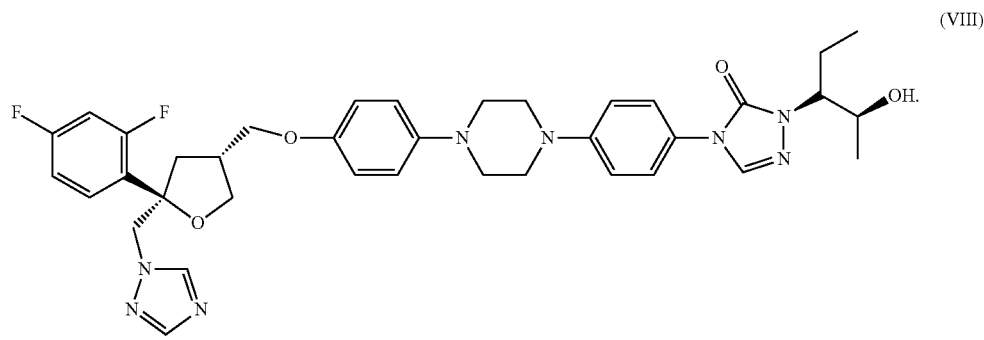

Also, the present invention relates to a process for the preparation of an antifungal agent, preferably of a compound of formula (VIII)

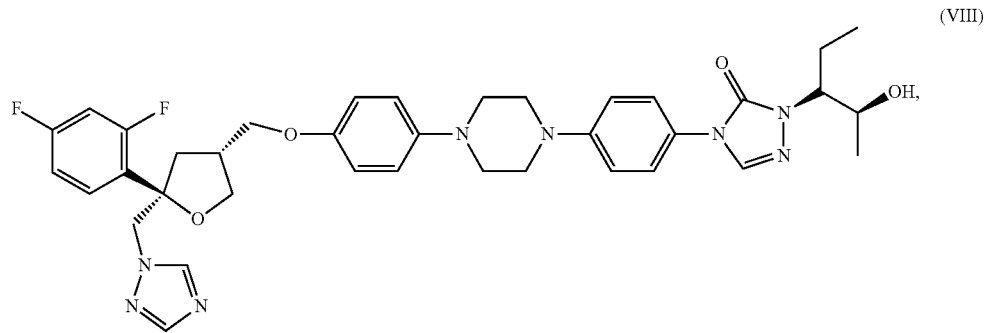

wherein an at least partially crystalline HCl salt of the compound of formula (I) as defined above containing at least 99% of the HCl salt of the cis-isomer according to formula (II)

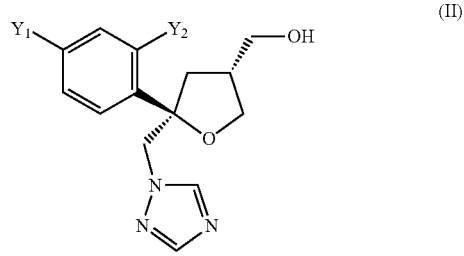

is used as a starting material, with both $Y_1$ and $Y_2$ are preferably being F.

In particular, the present invention relates to said use, or said method of using, or said process, comprising converting the HCl salt of the compound of formula (I) to the respective tosylate according to formula (IV)

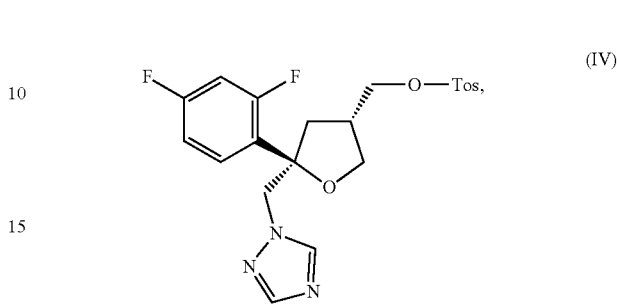

reacting the compound of formula (IV) with a compound of formula (V)

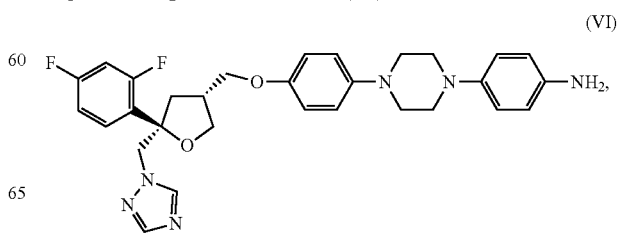

to give a compound of formula (VI)

and suitably reacting the compound of formula (VI) with a compound of formula (VII)

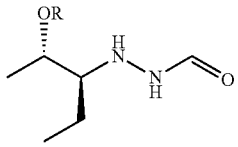
(VII)

to give the compound of formula (VIII), wherein R in the compound of formula (VII) is H or a suitable hydroxyl protecting group preferably selected from the group consisting of —$SiR_{aa}R_{bb}R_{cc}$ and optionally substituted alkyl, aryl, alkaryl or aralkyl residues, where $R_{aa}$, $R_{bb}$ and $R_{cc}$ are the same or different and selected from the group consisting of optionally suitably substituted alkyl and aryl residues, R preferably being H.

As far as converting the HCl salt of the compound of formula (I) to the respective tosylate according to formula (IV)

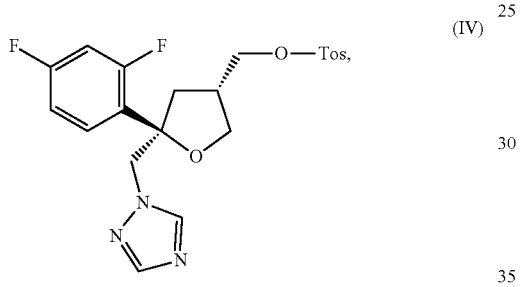
(IV)

is concerned, no particular restrictions exist. According to a preferred embodiment of the present invention, the at least partially crystalline, preferably crystalline salt of the compound of formula (I) is provided suspended in a suitable liquid, most preferably dichloromethane (DCM). To this suspension, preferably at least one suitable organic nitrogen base such as triethylamine (TEA) and/or 4-dimethylaminopyridine (DMAP) is/are added. To the resulting mixture, a suitable p-toluenesulfonyl containing compound such as p-toluenesulfonyl chloride (TsCl) is added at a preferred temperature of from 10 to 40° C. and preferably reacted for 1 to 6 hours. The obtained reaction mixture containing the compound of formula (IV) is preferably suitably extracted, and from the obtained organic layer, optionally after suitable concentration, the compound of formula (IV) is obtained as solid which may be optionally suitably dried and preferably subsequently, without any further intermediate treatment, employed as starting material for the reaction with the compound of formula (V) as described above.

Compared to the prior art, the considerably simplified process for the purification according to the present invention via preparation of the inventive HCl salt of compound of formula (I) with increased cis:trans ratio allows for directly employing the tosylate according to formula (IV) for the preparation of the compound of formula (VI) without the complicated purification of the tosylate by column chromatography. Thus, by suitably preparing the novel HCl salt of the compound of formula (I) according to the present invention, the overall process for the preparation of an antifungal agent, in particular posaconazole, is simplified, especially as far as the preparation of larger amounts is concerned.

Consequently, the present invention also relates to the use of the process for preparing a hydrogen chloride (HCl) salt of a compound of formula (I) as defined above for the purification of a diasteromeric mixture of the cis-isomer of formula (II) and the trans-isomer of formula (III)

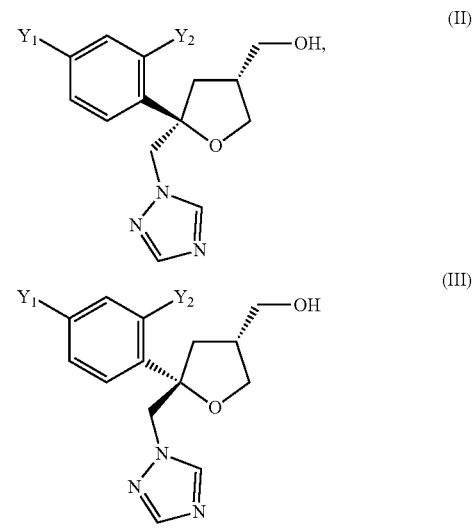

with regard to the cis-isomer, preferably for the purification of said diasteromeric mixture containing from 80 to 95%, preferably from 85 to 95% of the cis-isomer of formula (II) and from 20 to 5%, preferably from 15 to 5% of the trans-isomer of formula (III) to obtain a purified mixture containing at least 97%, preferably at least 98% and more preferably at least 99% of the HCl salt of the cis-isomer of formula (II) and at most 3%, preferably at most 2% and more preferably at most 1% of the HCl salt of the trans-isomer of formula (III).

The present invention is further illustrated by the following examples.

EXAMPLES

Example 1

Preparation of the Compound of Formula (I)

(a) Preparation of the Compound of Formula (Ba)

In 20 ml of MTBE, 3.8 g of Mg were suspended. The temperature of the suspension was 55° C. Then, 0.5 g of Grignard reagent $(CH_3)_3Si$—$CH_2MgCl$ in MTBE from a previous batch were added in order to dry the system (if no such Grignard reagent is available for the first batch, $(CH_3)_3Si$—$CH_2MgCl$ in diethyl ether (CAS Registry Number: 13170-43-9) commercially available as 1.0 M solution from Sigma-Aldrich can be used), followed by 1.0 ml of chloromethyl trimethyl silane (CM-TMS; CAS Registry Number: 2344-80-1; commercially available from Sigma-Aldrich). A solution of 14 ml of the CM-TMS in 43 ml of MTBE was added slowly over a period of 2 hours at a temperature of 55° C. The mixture was stirred for 2 hours at 55° C. and then cooled to a temperature of −10° C. Subsequently, 10.0 g of the commercial compound of formula (Aa) (CAS Registry Number: 51336-94-8; commercially available from Sigma-Aldrich) in 30 ml of MTBE were added and the temperature was kept in the range of from 0 to −10° C. The reaction mixture was quenched in a 20% (w/v) aqueous solution of ammonium chloride. The obtained organic layer was washed with a 20%

(w/v) aqueous solution of ammonium chloride. The thus washed organic layer was then washed with water.

To the organic layer, 11.0 ml of concentrated sulphuric acid were added, and the temperature was kept at 25 to 30° C. Then, the reaction mixture was stirred at a temperature of from 45 to 50° C. for 3 hours. Subsequently, the reaction mixture was cooled to 20° C. and 25 ml of water were added, and the organic layer was separated. The obtained organic layer was extracted with an 9% (w/v) aqueous solution of sodium bicarbonate, followed by washing with water. The solvents of the washed organic layer were removed by distillation under reduced pressure, and the compound of formula (Ba) was obtained as an oil.

The yield was 9.4 g, corresponding to a theoretical value of 95%.

(b) Preparation of the compound of formula (C) with $Y_1=Y_2=F$ and $R_1=R_2=CH_2CH_3$ 10.0 g of the compound of formula (Ba) (as oil, as obtained according to (a)) were dissolved in 20 ml of DMSO under stirring. Then, 3.2 g of NaOH flakes and 24.0 ml of diethyl malonate were added. The resulting suspension was stirred for 5 hours at 25 to 30° C. Subsequently, 100 ml of water were added, and the resulting mixture was stirred for 30 min. The thus obtained solution was extracted with 80 ml of cyclohexane at 25 to 30° C. After separation of the layers the aqueous layer was extracted with 40 ml of cyclohexane at 25 to 30° C. The combined organic layers were washed with a 5% (w/v) aqueous solution of NaOH, followed by washing with water. After washing, the solvents of the organic layer were removed by distillation under reduced pressure and the title compound was obtained as an oil.

The yield was 15.0 g, corresponding to a theoretical value of 90.0%.

(c) Preparation of the Compound of Formula (D) with $Y_1=Y_2=F$ 10.0 g of the compound of formula (C) as oil, as obtained according to (b), were dissolved in 120 ml of isopropyl alcohol and 13.0 ml of water under stirring at 25 to 30° C. The resulting mixture was cooled to a temperature of from 0 to −5° C. Then, 2.3 g of lithium chloride and 2.1 g of sodium borohydride were added at 0 to −5° C. The resulting suspension was stirred at 25 to 30° C. for 20 hours. The pH of the stirred mixture was adjusted to a value of 1 (measured by using a calibrated pH meter) by addition of 4 N aqueous HCl. Afterwards, an 20% (w/v) aqueous solution of NaOH was added to adjust the pH to a value of 10 (measured by using a calibrated pH meter). The resulting mixture was stirred for 1 hour. Then, the lower aqueous layer was drained. From the separated organic layer, the isopropyl alcohol was distilled off, and an oil was obtained. To the oil, 100 ml of toluene and 100 ml of water were added, and the product was extracted into the toluene layer. The solvents of the resulting toluene layer were removed by distillation, under reduced pressure and the compound of formula (D) with $Y_1=Y_2=F$ was obtained as oil.

The yield was 6.0 g, corresponding to a theoretical value of 82.0%.

(d) Preparation of the Compound of Formula (E) with $Y_1=Y_2=F$ 10.0 g of the compound of formula (D) as oil, as obtained according to (c), were dissolved in 80 ml of toluene and cooled to −15° C. Then, 7.4 g of sodium bicarbonate, 0.5 g of enzyme (Novo SP 435; *Candida antarctica*, Novozym 435 from Novo Nordisk), and 7.9 ml of isobutyric anhydride were added. The resulting mixture was stirred at −15° C. for 24 hours. Then the solids were filtered off and the filtrate was washed with an 5% (w/v) aqueous solution of sodium bicarbonate, followed by washing with water. The solvents of the resulting organic layer were removed by distillation under reduced pressure to obtain the desired product as an oil. This oil was dissolved in 40 ml of n-heptane at 50 to 60° C. The clear solution was gradually cooled to a temperature of 10° C. The compound of formula (E) with $Y_1=Y_2=F$ crystallized as colorless crystals. The obtained solids were filtered, and the wet filter cake was washed with 20 ml of n-heptane. The filter cake was then dried at 40° C. in vacuo and the compound of formula (E) with $Y_1=Y_2=F$ was obtained as colorless crystals.

The yield was 9.2 g, corresponding to a theoretical value of 70.0%.

(e) Preparation of the Compound of Formula (F) with $Y_1=Y_2=F$ and Hal=I 10.0 g of the crystals obtained in (d) were dissolved in 80 ml of ethyl acetate under stirring. The resulting solution was cooled to −15° C., and 21.5 g of iodine and 7.0 g of sodium bicarbonate were added. The obtained suspension was stirred at −15° C. for 5 hours. The reaction mixture was quenched in 200 ml of a 10% (w/v) aqueous solution of sodium sulphite. The organic layer was washed with 100 ml of a 10% (w/v) aqueous solution of sodium sulphite, followed by washing with water. The solvents of the thus obtained, washed organic layer were removed by distillation under reduced pressure to obtain the title compound as an oil.

The yield was 13.5 g, corresponding to a theoretical value of 95.0%.

(f) Preparation of the Compound of Formula (I) with $Y_1=Y_2=F$ 10.0 g of the compound of formula (F) as oil, as obtained according to (e), were dissolved in 80 ml of DMSO under stirring. Then, 10 g of the sodium salt of 1,2,4-triazole were added at 25 to 30° C., and the resulting reaction mixture was stirred for 24 hours at 85 to 90° C. The mixture was then cooled to 25 to 30° C., and 25 ml of 5% (w/v) aqueous solution of sodium hydroxide were added. The mixture was then stirred for 3 hours at 25 to 30° C. 100 ml of water were added, and the product was extracted into 150 ml of methyl tetrahydrofuran. The thus obtained organic layer was washed with a 10% (w/v) aqueous solution of sodium chloride, and subsequently the solvents of the resulting separated organic layer were removed by distillation under reduced pressure to obtain the compound of formula (I) with $Y_1=Y_2=F$ as a crude oil.

The yield was 6.0 g, corresponding to a theoretical value of 86.0%.

10.0 g of the crude oil were dissolved in 100 ml of methyl tetrahydrofuran under stirring at 50 to 60° C. Then, 300 ml of n-heptane were added at 50 to 60° C. over a period of 30 min. The turbid solution was cooled to 25 to 30° C. and stirred for another 30 min. The resulting suspension was cooled to 0 to −5° C. and stirred for 2 hours. The product was filtered, and the wet cake was washed with 20 ml of n-heptane. The washed product was dried at 40° C. in vacuo to obtain the crystalline compound of formula (I) with $Y_1=Y_2=F$ as a colorless solid. The yield was 7.0 g, corresponding to a theoretical value of 70.0%.

The compound of formula (I) with $Y_1=Y_2=F$ was obtained as mixture of the cis-isomer with the respective trans-isomer with a cis:trans ratio of 9:1.

Example 2

Preparation of an HCl Salt of Compound (I) with $Y_1$ and $Y_2=F$ without Solid Extraction, using HCl in THF as Second Solvent 5 g of the crystalline compound of formula (I) with $Y_1$ and $Y_2=F$ as obtained from Example 1 (16.9 mmol, cis:trans=

9:1) were dissolved in 75 ml of MIBK and heated to 60° C. Next, 7.2 ml of HCl in THF (23.8 mmol HCl; concentration=3.3 mol/l) were added in one portion. Then, the mixture was stirred for 60 min at 60° C. After about 5-10 min, the mixture became cloudy, and crystallization occurred. The thus obtained suspension was cooled to ambient temperature within 90 min. Stirring was continued for another 60 min at room temperature. The obtained solid was isolated by filtration, washed twice with MIBK (2×10 ml) and dried under vacuum at 45° C.

The HCl salt of compound of formula (I) with $Y_1$ and $Y_2$=F was obtained as colorless solid with a yield of 78%, corresponding to 3.95 g. The HCl salt of compound of formula (I) with $Y_1$ and $Y_2$=F contained the HCl salt of the cis-isomer of formula (II) with $Y_1$ and $Y_2$=F and the HCl salt of the trans-isomer of formula (III) with $Y_1$ and $Y_2$=F with a cis:trans ratio of 98.6:1.4, as determined by HPLC.

Example 3

Preparation of an HCl Salt of Compound (I) with $Y_1$ and $Y_2$=F without Solid Extraction, using HCl in THF as Second Solvent 20 g of the crystalline compound of formula (I) with $Y_1$ and $Y_2$=F as obtained from Example 1 (66.7 mmol, cis:trans= 9:1) were dissolved in 250 ml of MIBK and heated to 60° C. Next, 34 ml of HCl in THF (95.2 mmol HCl; concentration=2.8 mol/l) were added dropwise. Then, the mixture was stirred for 60 min at 60° C. After about 10 min, the mixture became cloudy, and crystallization occurred. The thus obtained suspension was cooled to ambient temperature within 90 min. Stirring was continued for another 60 min at room temperature. The obtained solid was isolated by filtration, washed with MIBK (10 ml) and dried under vacuum at 45° C.

The HCl salt of compound of formula (I) with $Y_1$ and $Y_2$=F was obtained as colorless solid with a yield of 60%, corresponding to 12.15 µg. The HCl salt of compound of formula (I) with $Y_1$ and $Y_2$=F contained the HCl salt of the cis-isomer of formula (II) with $Y_1$ and $Y_2$=F and the HCl salt of the trans-isomer of formula (III) with $Y_1$ and $Y_2$=F with a cis:trans ratio of 99.3:0.7, as determined by HPLC.

Example 4

Preparation of an HCl Salt of Compound (I) with $Y_1$ and $Y_2$=F without Solid Extraction, Using HCl in n-Butanol as Second Solvent 0.5 g of the crystalline compound of formula (I) with $Y_1$ and $Y_2$=F as obtained from Example 1 (1.6 mmol, cis:trans=9:1) were dissolved in 5 ml of n-butanol and heated to 60° C. Next, 386 µl of HCl in n-butanol (2.2 mmol HCl; concentration=5.7 mol/l) were added dropwise. Then, the mixture was stirred for 60 min at 60° C. The thus obtained suspension was cooled to ambient temperature. Stirring was continued for another 60 min at room temperature. The obtained white solid was isolated by filtration, washed with a small amount of diethyl ether and dried under vacuum at 45° C.

The HCl salt of compound of formula (I) with $Y_1$ and $Y_2$=F was obtained as colorless solid with a yield of 47%, corresponding to 241 mg. The HCl salt of compound of formula (I) with $Y_1$ and $Y_2$=F contained the HCl salt of the cis-isomer of formula (II) with $Y_1$ and $Y_2$=F and the HCl salt of the trans-isomer of formula (III) with $Y_1$ and $Y_2$=F with a cis:trans ratio of 98.6:1.4, as determined by HPLC.

$^1$H-NMR (300 MHz, CDCl$_3$) delta ppm 2.12-2.51 (m, 3H) 3.36-3.72 (m, 2H) 3.93-4.20 (m, 2H) 4.74 (d, J=14.05 Hz, 1H) 5.05 (d, J=13.81 Hz, 1H) 6.56-6.94 (m, 2H) 6.98-7.24 (m, 1H) 8.35-844 (m, 1H) 8.44-8.60 (m, 2H) 10.15 (s, 1H)
$^{13}$C-NMR (75 MHz, CDCl$_3$) delta ppm 38.1, 41.2, 58.0, 62.3, 70.6, 82.6, 104.6, 111.3, 125.2, 128.0, 141.9, 142.5, 161.2.

Example 5

Preparation of an HCl Salt of Compound (I) with $Y_1$ and $Y_2$=F with Acetone and HCl in MTBE 10.0 g of the compound of formula (I) as crude oil as obtained in Example 1 (f) prior to the crystallization were dissolved in 200 ml of acetone under stirring at 30 to 40° C. The resulting solution was cooled to 25 to 30° C. Then, HCl in MTBE (10 wt.-%) was added over a period of 15 min at 25 to 30° C. The solid crystallized when the mixture was stirred for 15 min. Then, 200 ml of MTBE were added slowly over a period of 30 min. The suspension was cooled to 0 to −5° C. and stirred for 2 hours. The product was filtered, and the wet cake was washed with 20 ml of MTBE. After drying at 70° C. in vacuo, the HCl salt of the compound (I) with $Y_1$=$Y_2$=F was obtained as colourless solid.

The yield was 9.5 g, corresponding to a theoretical value of 85.0%.

The HCl salt of compound of formula (I) with $Y_1$=$Y_2$=F was obtained as mixture of the cis-isomer with the respective trans-isomer with a cis:trans ratio of 9:1.

Example 6

Preparation of an HCl Salt of Compound (I) with $Y_1$ and $Y_2$=F with Solid Extraction, Using MIBK and n-Butanol as Solvent Mixture 20.0 g of the crystalline HCl salt of the compound of formula (I) with $Y_1$ and $Y_2$=F containing the HCl salt of the cis-isomer of formula (II) with $Y_1$ and $Y_2$=F and the HCl salt of the trans-isomer of formula (III) with $Y_1$ and $Y_2$=F with a cis:trans ratio of 9:1 (60 mmol) obtained as described above in Example 5 were suspended in a mixture of n-butanol (50 ml) and MIBK (50 ml). The mixture was heated to 60° C., and this temperature was maintained for a period of 2 hours. Subsequently, the mixture was cooled to room temperature. The obtained solid was filtered off and washed with a small amount of diethyl ether.

This solid (14.55 g, 43.9 mmol) was re-suspended in a mixture of n-butanol (36.4 ml) and MIBK (36.4 ml). The mixture was heated to 60° C., and this temperature was maintained for a period of 2 hours. Subsequently, the mixture was cooled to room temperature. The obtained solid was filtered off and washed with a small amount of diethyl ether.

After drying under vacuum at 45° C., the HCl salt of compound of formula (I) with $Y_1$ and $Y_2$=F was obtained as colorless crystalline solid with an overall yield of 66% over 2 steps, corresponding to 10.75 g. The crystals showed bifringing under the microscope. The HCl salt of compound of formula (I) with $Y_1$ and $Y_2$=F contained the HCl salt of the cis-isomer of formula (II) with $Y_1$ and $Y_2$=F and the HCl salt of the trans-isomer of formula (III) with $Y_1$ and $Y_2$=F with a cis:trans ratio of 99.2:0.8, as determined by HPLC.

HPLC Method for determination of purity and cis/trans ratio of compound of formula (I) with $Y_1$=$Y_2$=F:

| | |
|---|---|
| Principle | Determination by HPLC using UV detector |
| Reagents and Equipment | Potassium dihydrogen phosphate — Merck Cat. No. 60487305001730 |
| | Orthophosphoric acid (85%) — AR Grade e.g (Merck, Cat No. 61768205001046) |
| | Acetonitrile — HPLC grade (e.g. Merck Cat. No. 61830025001046) |
| | HPLC system — Agilent 1100 series or similar |
| | pH meter — e.g. Metrohm or equivalent |
| Buffer Preparation | Dissolve 2.72 g of Potassium dihydrogen phosphate in 1000 ml of water and adjust the pH to 3.0 ± 0.05 by adding dilute orthophosphoric acid (85%) using a pH meter. Filter through 0.45 μm (micrometer) filter and degas. |
| Diluent | Buffer: Methanol (80:20) v/v |

Chromatographic Conditions

| | |
|---|---|
| Column | $C_{16}$, 250 mm × 4.6 mm i.d.5 μ, e.g. Ascentis RP amide or equivalent column can be used after appropriate validation. |
| System | Gradient |
| Column Temperature | 40° C. |
| Mobile phase A | Buffer |
| Mobile phase B | Buffer: Acetonitrile (30:70) v/v |
| Flow rate | 2.0 ml/min |
| Injection temperature | 25° C. |
| Injection volume | 25 μl (microliter) |
| Run time | 45 minutes |
| Detection wavelength | 210 nm |
| System | Gradient |

| Gradient program | Time | % mobile phase B |
|---|---|---|
| | 0 | 20 |
| | 5 | 20 |
| | 15 | 40 |
| | 25 | 80 |
| | 28 | 90 |
| | 39 | 90 |
| | 41 | 20 |
| | 45 | 20 |

The X-ray powder diffraction pattern (XRD) of this compound of formula (I) with Y1=Y2=F is shown in FIG. 1.

Method for the Recording of X-Ray Diffractograms:

The samples were analysed on the Zero background holder in spinning mode at ambient conditions. A typical precision of the 2-Theta values is in the range of about ±0.2° 2-Theta. Thus a diffraction peak that appears at 8.6° 2-Theta can appear between 8.4 and 8.8° 2-Theta on most X-ray diffractometers under standard conditions.

Instrument Parameters:

XRD Measurement Conditions:

| | |
|---|---|
| Instrument | X'PERT PRO PANalytical |
| Scan Axis | Gonio |
| Start Position [°2 Th.] | 3.0 |
| End Position [°2 Th.] | 40.0 |
| Step Size [°] | 0.0170 |
| Scan Step Time [s] | 100 |
| Scan Type | Continuous |
| Anode Material | Cu |
| Generator Settings | 45 kV, 40 mA |
| Spinning | Yes |

Incident Beam Optics

| | |
|---|---|
| Soller Slits | 0.02 radians |
| Divergence Slit Type | Programmable Slits (Fixed 0.5°) |

Incident Beam Optics

| | |
|---|---|
| AntiScatter Slits | Fixed Slits (1°) |
| Beam Mask | 10 mm (MPD/MRD) |

Diffracted Beam Optics

| | |
|---|---|
| Antiscatter Slit | Programmable Slits (Fixed 0.5°) |
| Soller Slits | 0.02 radians |
| Filter | Nickel |
| Detector | X'celerator |
| Mode | Scanning |
| Active Path Length | 2.122° |

LIST OF CITED DOCUMENTS

U.S. Pat. No. 5,403,937
EP 0 736 030 A1
WO 95/17407 A1
WO 94/25452 A1
WO 97/22710
Tetrahedron Letters 32 (1991), pp. 7545-7548

The invention claimed is:

1. A process for the preparation of a hydrogen chloride (HCl) salt of a compound of formula (I)

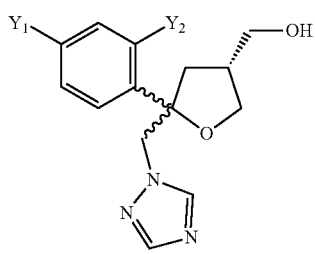

(I)

wherein $Y_1$ and $Y_2$ are independently F or Cl, said compound of formula (I) containing the cis-isomer of formula (II) and the trans-isomer of formula (III)

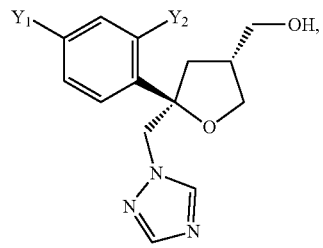

(II)

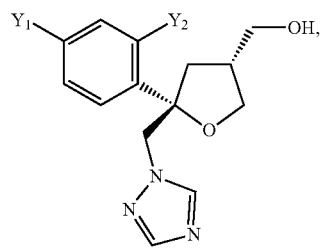

(III)

the process comprising (1) providing the compound of formula (I) comprised in a first solvent;

(2) treating the compound of formula (I) comprised in the first solvent with HCl comprised in a second solvent to obtain the HCl salt of the compound of formula (I);

after (2), at least partially crystallizing the HCl salt of compound of formula (I);

(2b) separating the at least partially crystallized HCl salt of compound of formula (I); and (3) subjecting the at least partially crystallized HCl salt of compound of formula (I) to solid extraction in a solvent to obtain the HCl salt of compound of formula (I), thereby increasing the content with regard to the HCl salt of the cis-isomer of formula (II), wherein the at least partially crystallized HCl salt of compound of formula (I) obtained from (3) contains at least 97% of the HCl salt of the cis-isomer of formula (II) and at most 3% of the HCl salt of the trans-isomer of formula (III).

2. The process of claim 1, wherein in (1), the compound of formula (I) is provided by a method comprising (i.1) reacting a compound of formula (A)

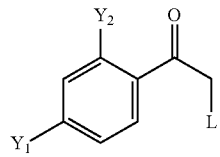

(A)

wherein L is a leaving group, in a solvent with a nucleophilic compound comprising a nucleophilic residue $R_aR_bR_cSi$—$CH_2$ wherein $R_a$, $R_b$ and $R_c$ are the same or different and selected from the group consisting of optionally substituted alkyl and aryl residues, to obtain a reaction mixture containing as intermediate a beta-hydroxy silane of formula

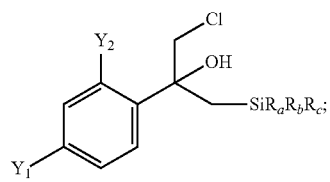

(i.2) treating the resulting reaction mixture, with a reagent, promoting an elimination reaction to obtain a reaction mixture containing a compound of formula (B)

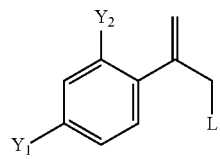

(B)

wherein treating is performed at a temperature in the range of from −20 to +70° C.;

(ii) reacting the compound of formula (B) with a malonic ester $R_1OOC$—$CH_2$—$COOR_2$ to obtain a compound of formula (C)

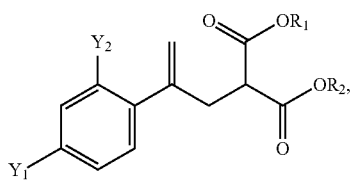

(C)

wherein $R_1$ and $R_2$ are independently an optionally suitably substituted alkyl group having from 1 to 5 carbon atoms, wherein, after (ii) and before (iii), the compound of formula (C) is optionally separated by extraction in a solvent;

(iii) reducing the compound of formula (C) to obtain a compound of formula (D)

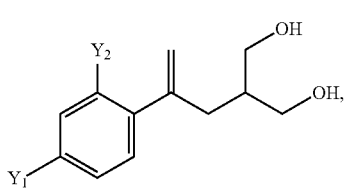

the reducing agent in an amount of at most 2 molar equivalents with respect to the compound of formula (C);

(iv) acylating the compound of formula (D) with isobutyric anhydride to obtain a compound of formula (E)

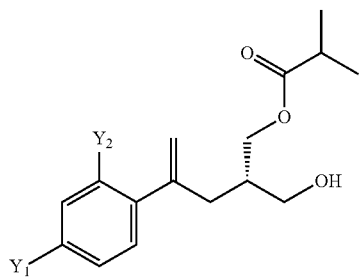

wherein after (iv) and before (v), the compound of formula (E) is at least partially crystallized;

(v) reacting the compound of formula (E) with a halogen $Hal_2$ selected from the group consisting of $Cl_2$, $Br_2$ and $I_2$, in the presence of a base in a solvent to obtain a compound of formula (F)

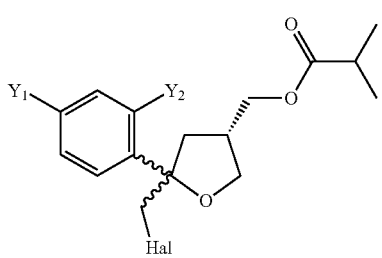

wherein from 80 to 95% of the molecules of compound (F) are present as cis-isomer of formula (Fa)

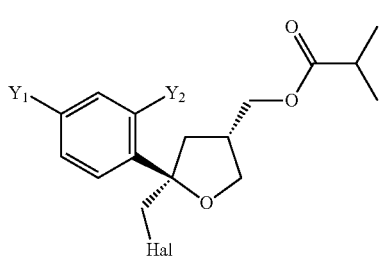

and from 20 to 5% of the molecules of compound (F) are present as trans-isomer of formula (Fb)

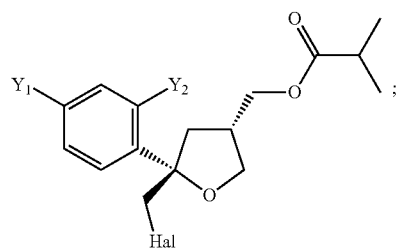

(vi.1) heating the compound of formula (F) at a temperature in the range of from +70 to +100° C. in a solvent with a 1,2,4-triazole alkali metal salt, and treating the resulting reaction mixture with a base suitable to promote saponification of the ester moiety in the presence of methanol, to obtain a compound of formula (I)

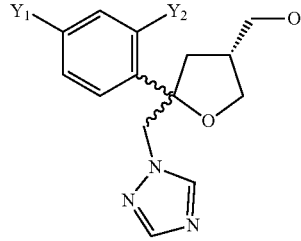

(vi.2) separating the compound of formula (I) from the reaction mixture obtained from (vi.1) by extraction in a solvent.

3. The process of claim 2, wherein the method according to which the compound of formula (I) is provided in (1) further comprises (vii) at least partially crystallizing the compound of formula (I) after (vi.2).

4. The process of claim 1, wherein the first solvent in which the compound of formula (I) is dissolved comprises an organic solvent.

5. The process of claim 1, wherein the first solvent in which the compound of formula (I) is comprised is selected from the group consisting of ethyl acetate, isopropyl acetate, diethyl ether, tetrahydrofuran (THF), methyl tetrahydrofuran, dioxane, methanol, n-propanol, 1-butanol, 2-butanol, 2-methyl-1-butanol, 3-methyl-1-butanol, acetone, 2-butanone, and methyl isobutyl ketone (MIBK), and wherein the second solvent is selected from the group consisting of dioxane, tetrahydrofuran (THF), diethyl ether, diisopropyl ether, methyl tert-butyl ether (MTBE), ethyl acetate, methanol, n-propanol, 1-butanol, 2-butanol, 2-methyl-1-butanol, 3-methyl-1-butanol, and toluene.

6. The process of claim 4, wherein the first and/or the second solvent comprise(s) an alcohol and/or a precursor of an alcohol.

7. The process of claim 6, wherein the first solvent is tetrahydrofuran, methyl isobutyl ketone and the second solvent is, or wherein both the first and the second solvent is n-butanol.

8. The process of claim 6, wherein treating in (2) is carried out at a temperature in the range of from 20 to 100° C.

9. The process of claim 6, wherein in (2), HCl comprised in the second solvent is employed relative to the compound of formula (I) in a molar ratio HCl:(I) in the range of from 1.0:1 to 2.0:1.

10. The process of claim 1, wherein treating in (2) is carried out at a temperature in the range from 0 to 100° C. and wherein in (2), HCl comprised in the second solvent is employed relative to the compound of formula (I) in a molar ratio HCl:(I) in the range of from 1.0:1 to 3.0:1.

11. The process of claim 1, wherein the solvent of step (3) is methyl isobutyl ketone or a mixture of methyl isobutyl ketone and an alcohol, being in the range of from 0.5:1 to 10:1.

12. The process of claim 1, wherein the solid extraction is carried out at a temperature in the range of from 20 to 100° C.

13. The process of claim 1, wherein in (3), the concentration of the HCl salt of compound of formula (I) is in the range of from 0.25 to 0.75 mol/liter solvent.

14. The process of claim 1, further comprising, after (3), isolating the at least partially crystallized HCl salt of compound of formula (I).

15. The process of claim 1, further comprising
    (3a) isolating the at least partially crystallized HCl salt of compound of formula (I) from the mixture obtained from (3), optionally followed by washing with a solvent.

16. The process of claim 15, further comprising subjecting the HCl salt obtained from (3a) to solid extraction.

17. A crystalline hydrogen chloride (HCl) salt of a compound of formula (I)

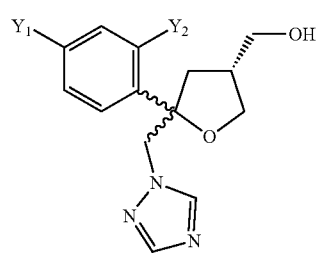

wherein $Y_1$ and $Y_2$ are independently F or Cl, said compound of formula (I) containing the cis-isomer of formula (II) and the trans-isomer of formula (III)

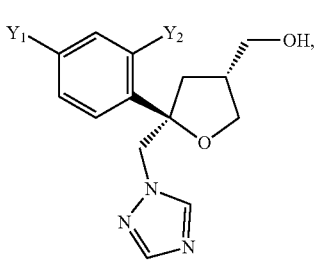

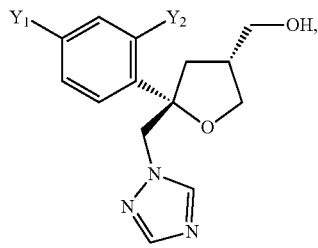

containing at least 97% of the HCl salt of the cis-isomer of formula (II) and at most 3% of the HCl salt of the trans-isomer of formula (III).

18. The process of claim 1, wherein $Y_1$ and $Y_2$ are F.

19. The process of claim 4, wherein the organic solvent is an alcohol and/or a precursor of an alcohol, an ether, a ketone, an ester, or a mixture of two or more thereof.

20. The process of claim 1, wherein the at least partially crystallized HCl salt of compound of formula (I) contains at least 98% of the HCl salt of the cis-isomer of formula (II) and at most 2% of the HCl salt of the trans-isomer of formula (III).

21. The process of claim 1, wherein the at least partially crystallized HCl salt of compound of formula (I) contains at least 99% of the HCl salt of the cis-isomer of formula (II) and at most 1% of the HCl salt of the trans-isomer of formula (III).

22. The process of claim 1, wherein the separating the at least partially crystallized HCl salt of compound of formula is by filtration, optionally followed by washing with a solvent.

23. The process of claim 1, wherein the solvent of step (3) is methyl iso-butyl ketone.

24. The process of claim 10, wherein the molar ratio HCl:(I) is in the range of from 1.5:1 to 2.5:1.

25. The process of claim 10, wherein the molar ratio HCl:(I) is in the range of from 2.0:1 to 2.2:1.

26. The process of claim 11, wherein the molar ratio of methyl isobutyl ketone relative to the alcohol is in the range of from 0.75:1 to 5:1.

27. The process of claim 11, wherein the molar ratio of methyl isobutyl ketone relative to the alcohol is in the range of from 0.95:1 to 1.05:1.

28. The process of claim 11, wherein the alcohol is n-butanol.

29. The process of claim 12, wherein the solid extraction is carried out at a temperature in the range of from 40 to 80° C.

30. The process of claim 12, wherein the solid extraction is carried out at a temperature in the range of from 55 to 65° C.

31. The process of claim 13, wherein the range is from 0.55 to 0.65 mol/liter solvent.

32. The process of claim 15, wherein the isolating the at least partially crystallized HCl salt of compound of formula (I) from the mixture obtained from (3) is by filtration.

33. The process of claim 15, wherein the solvent is diethyl ether or methyl tert-butyl ether.

34. The process of claim 16, wherein the solid extraction is followed by separating the thus obtained HCl salt according to the process of claim 15.

35. The crystalline hydrogen chloride (HCl) salt of claim 17, wherein $Y_1$ and $Y_2$ are independently F.

36. The crystalline HCl salt of claim 17, containing at least 98% of the HCl salt of the cis-isomer of formula (II) and at most 2% of the HCl salt of the trans-isomer of formula (III).

37. The crystalline HCl salt of claim 17, containing at least 99% of the HCl salt of the cis-isomer of formula (II) and at most 1% of the HCl salt of the trans-isomer of formula (III).

* * * * *